(12) United States Patent
Collins et al.

(10) Patent No.: US 7,144,903 B2
(45) Date of Patent: Dec. 5, 2006

(54) CCR4 ANTAGONISTS

(75) Inventors: Tassie Collins, San Mateo, CA (US); Hossen Mahmud, San Antonio, TX (US); Jonathan Houze, San Mateo, CA (US); Alan Xi Huang, San Mateo, CA (US); Julio C. Medina, San Carlos, CA (US); Xuemei Wang, San Mateo, CA (US); Feng Xu, Palo Alto, CA (US); Qingge Xu, Burlingame, CA (US); Liusheng Zhu, Burlingame, CA (US)

(73) Assignee: Amgen Inc., Thousand Oaks, CA (US)

( * ) Notice: Subject to any disclaimer, the term of this patent is extended or adjusted under 35 U.S.C. 154(b) by 102 days.

(21) Appl. No.: 10/155,605

(22) Filed: May 22, 2002

(65) Prior Publication Data

US 2003/0018022 A1    Jan. 23, 2003

Related U.S. Application Data

(60) Provisional application No. 60/293,781, filed on May 23, 2001.

(51) Int. Cl.
*C07D 417/12* (2006.01)
*C07D 419/12* (2006.01)
*C07D 401/00* (2006.01)
*A61K 31/425* (2006.01)

(52) U.S. Cl. .................. 514/365; 548/181; 544/137; 546/209

(58) Field of Classification Search ................ 548/181; 514/365
See application file for complete search history.

(56) References Cited

U.S. PATENT DOCUMENTS

| | | | |
|---|---|---|---|
| 2,863,874 | A | 12/1958 | Gregory |
| 3,201,409 | A | 8/1965 | Spivack et al. |
| 3,228,888 | A | 1/1966 | Spivack et al. |
| 3,467,666 | A | 9/1969 | Dexter et al. |
| 3,896,223 | A | 7/1975 | Ariyan et al. |
| 4,275,210 | A | 6/1981 | Paget, Jr. |
| 4,826,990 | A | 5/1989 | Musser et al. |
| 5,919,776 | A | 7/1999 | Hagmann et al. |
| 6,207,665 | B1 | 3/2001 | Bauman et al. |
| 6,426,360 | B1 | 7/2002 | Weier et al. |
| 6,436,967 | B1 | 8/2002 | Talley et al. |
| 6,498,161 | B1 | 12/2002 | Caldwell et al. |
| 6,706,767 | B1 | 3/2004 | Saxena et al. |
| 6,784,195 | B1 | 8/2004 | Hale et al. |
| 2002/0173524 | A1 | 11/2002 | Collins et al. |
| 2003/0018022 | A1 | 1/2003 | Collins et al. |
| 2004/0039035 | A1 | 2/2004 | Collins et al. |

FOREIGN PATENT DOCUMENTS

| | | |
|---|---|---|
| EP | 0 310 370 | 4/1989 |
| EP | 1 050 307 A1 | 11/2000 |
| EP | 01 98 1850 | 3/2005 |
| WO | WO 99/04794 A1 | 2/1999 |
| WO | WO 99/38514 A1 | 8/1999 |
| WO | WO 99/38845 A1 | 8/1999 |
| WO | WO 99/42455 A1 | 8/1999 |
| WO | WO 00/41724 A1 | 7/2000 |
| WO | WO 00/42074 A1 | 7/2000 |
| WO | WO02/030357 | 4/2002 |
| WO | WO 02/30358 A2 | 4/2002 |
| WO | WO 02/34745 A1 | 5/2002 |

OTHER PUBLICATIONS

Das, et al., "Thiazole derivatives as possible fungicides. I, 2-(Substituted amino)-4,5-dimethylthiazoles" Chemical Abstracts 49:11626c (1955).

Fernandes, et al., "Chemotherapy of malaria. II. Synthesis of some thiazole derivatives" Chemical Abstracts 48:4513g (1954).

Mahapatra, et al., "Prepn. of N-substituted 2-aminothiazoles. III. Condensation of propyl methyl ketone with substituted thio-ureas" Chemical Abstracts 50:962h (1956).

Mahapatra, et al., "Separation of isomeric ureas and oxazoles by thin-layer chromatography" 193(2):338-339.

Nayak, et al., "Synthesis, fungicidal, antispasmodic, and antihistaminic activity of some 2-substituted thiazoles" Chemical Abstracts 114:23843 (1991).

Pascual, "Preparation of substituted 2-aminooxazole-4-carbonitriles" Helv. Chim. Acta. 72(3):556-569 (1989).

Tripathy, et al., "Paper and thin-layer chromatographic studies on the separation of mixtures of isomeric mono and diaryl thioureas, thiazoles, and thiazolines" Chemical Abstracts 80:27161 (1974).

National Institutes of Health, Web Page (http://www.csr.nih.gov/review/cvsirg.htm) referring to atherosclerosis as chronic inflammatory disease at p. 14 (Jun. 29, 2004).

Sun, et al. "Cytokine-induced enhancement of autoimmune inflammation in the brain and spinal cord: implications for multiple sclerosis" Neuropathol Appl Neurobiol. 2004 Aug.; 30(4): 374-84.

Muller, et al., "Chemokines and chemokine receptors: potential therapeutic targets in multiple sclerosis" Curr Drug Targets Inflamm. Allergy. 2004 Sep.; 3(3):279-90.

(Continued)

*Primary Examiner*—Johann Richter
*Assistant Examiner*—Ebenezer Sackey
(74) *Attorney, Agent, or Firm*—Jones Day

(57) ABSTRACT

Compounds, compositions and methods are provided that are useful in the treatment of chemokine receptor-mediated conditions and diseases. In particular, the invention provides compounds which modulate CCR4 function or a CCR4-mediated response. The subject compounds and compositions are useful for the treatment or prevention of inflammatory conditions and diseases.

44 Claims, 1 Drawing Sheet

OTHER PUBLICATIONS

Imai, et al. "Macrophage-derived Chemokine Is a Functional Ligand for the CC Chemokine Receptor 4" J. Biol. Chem. 273:1764-1768 (1998).

Imai, et al. "The T-Cell-directed CC Chemokine TARC Is a Highly Specific Biological Ligand for CC ChemokineReceptor 4" J. Biol. Chem. 272:15036-15042 (1997).

Kita, et al. "Chemokines Active on Eosinophils: Potential Roles in Allergic Inflammation" J. Exp. Med. 183, 2421-2426 (1996).

Baggiolini "Chemokines and leukocyte traffic" Nature 392:565-8 (1998).

Baggiolini, et al. "Blocking ChemokineReceptors" J. Exp. Med. 186:1189-1191 (1997).

CCR4 ANTAGONISTS

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165–183 (1991), Schall, et al., *Curr. Opin. Immunol.*, 6:865–873 (1994) and Murphy, *Rev. Immun.*, 12:593–633 (1994)). In addition to stimulating chemotaxis, chemokines can selectively induce other changes in responsive cells, including changes in cell shape, transient rises in the concentration of intracellular free calcium ions ($[Ca^{2+}]_i$, granule exocytosis, integrin upregulation, formation of bioactive lipids (e.g., leukotrienes) and respiratory burst associated with leukocyte activation. Thus, the chemokines are early triggers of the inflammatory response, causing inflammatory mediator release, chemotaxis and extravasation to sites of infection or inflammation.

There are four classes of chemokines, CXC ($\alpha$), CC ($\beta$), C($\gamma$), and $CX_3C$ ($\delta$), depending on whether the first two cysteines are separated by a single amino acid (C—X—C), are adjacent (C—C), have a missing cysteine pair (C), or are separated by three amino acids ($CX_3C$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381:661–666 (1996)). The C chemokine lymphotactin shows specificity for lymphocytes (Kelner, et al., *Science*, 266:1395–1399 (1994)) while the $CX_3C$ chemokine fractalkine shows specificity for lymphocytes and monocytes (Bazan, et al., *Nature*, 385:640–644 (1997).

Chemokines bind to specific cell-surface receptors belonging to the family of G-protein-coupled seven-transmembrane-domain proteins (reviewed in Horuk, *Trends Pharm. Sci.* 15:159–165 (1994)) which are termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") to MIP-1$\alpha$, MIP-1$\beta$, MCP-3, RANTES (Ben-Barruch, et al., *J. Biol. Chem.*, 270:22123–22128 (1995); Neote, et al., *Cell*, 72:415–425 (1993)); CCR2A and CCR2B (or "CKR-2A"/"CKR-2A" or "CC-CKR-2A"/"CC-CKR2A") to MCP-1, MCP-3, MCP-4; CCR3 (or "CKR-3" or "CC-CKR-3") to eotaxin, RANTES, MCP; (Ponath, et al., *J. Exp. Med.*, 183:2437–2448 (1996)); CCR4 (also referred to as "CKR-4","CC-CKR-4" or "CMKBR4"), to TARC, MDC (Imai et al. (1998) *J. Biol. Chem.* 273:1764–1768); CCR5 (or "CKR-5" or "CC-CKR-5") to MIP-1$\alpha$, RANTES, MIP-1$\beta$ (Sanson, et al., *Biochemistry*, 35:3362–3367 (1996)); CCR6 to MIP-3 alpha (Greaves, et al., *J. Exp. Med.*, 186:837–844 (1997)); CCR7 to MIP-3 beta and 6Ckine (Campbell, et al., *J. Cell. Biol.*, 141:1053–1059(1998)); CCR8 to 1-309, HHV8 vMIP-I, HHV-8 vMIP-II, MCV vMCC-I (Dairaghi, et al., *J. Biol. Chem.*, 274:21569–21574 (1999)); CCR9 to TECK (Zaballos, et al., *J. Immunol.*, 162:5671–5675 (1999)), D6 MIP-1 beta, RANTES, and MCP-3 (Nibbs, et al., *J. Biol. Chem.*, 272:32078–32083 (1997)), the Duffy blood-group antigen to IL-8, Gro$\alpha$, RANTES, MCP-1 (Chaudhun et al. (1994) *J. Biol. Chem.* 269:7835–7838, Murphy et al. (2000) *Pharm. Rev.* 52:145–176) and CCR10 to CTACK, CCL28 (Jarmin et al. (2000) *J. Immunol.* 164:3460–3464, Homey et al. (2000) *J. Immunol.* 164:3465–3470, Wang et al. (2000) *J. Biol. Chem.* 275:22313–22323).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, $CX_3CR1$ and XCR1 have been implicated as being important mediators of inflammatory and immunoregulatory disorders and diseases, including asthma and allergic diseases, as well as autoimmune pathologies such as rheumatoid arthritis and atherosclerosis.

The CCR4 chemokine receptor, first identified by Power et al. (Power et al. (1995) *J. Biol. Chem.* 270:19495–19500), is expressed primarily in peripheral blood T lymphocytes. CCR4 is involved in T lymphocyte homing to the skin and lungs (see, e.g., Campbell et al. (1999) *Nature* 400:776–780, Gonzalo et al. (1999) *J. Immunol.* 163:403–411, Lloyd et al. (2000) *J. Exp. Med.* 191:265–273, Kawasaki et al. (2001) *J. Immunol.* 166:2055–2062).

The identification of compounds that modulate the function of CCR4 represents an attractive approach to the development of therapeutic agents for the treatment of inflammatory conditions and diseases associated with CCR4 activation, such as psoriasis, asthma and allergic diseases.

SUMMARY OF THE INVENTION

The present invention is directed to compounds which are modulators of CCR4 chemokine receptor function and are useful in the prevention or treatment of inflammatory conditions and diseases such as allergic diseases, psoriasis, atopic dermatitis and asthma. The invention is also directed to pharmaceutical compositions comprising these compounds and the use of these compounds and compositions in the prevention or treatment of diseases in which CCR4 chemokine receptors are involved.

More particularly, the compounds provided herein have the general formula (I):

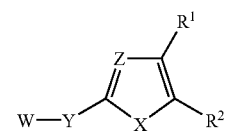

wherein W is selected from the group consisting of aryl, heteroaryl, ($C_{1-8}$)alkyl, heteroalkyl, cycloalkyl and heterocycloalkyl; X is selected from the group consisting of $N(R^5)$, S, O, $C(R^3)$=$C(R^4)$, N=$C(R^4)$ and optionally, when Z is N, X can be $C(R^6)(R^7)$; Y is selected from the group consisting of a bond, $N(R^5)$, $N(R^5)$—($C_1$–$C_8$)alkylene, O, S and $S(O)_n$, wherein the integer n is 1 or 2; and Z is selected from the group consisting of N and $C(R^8)$. $R^1$ and $R^2$ are independently selected from the group consisting of H, halogen, CN, $CO_2R'$, CONR'R", ($C_1$–$C_8$)alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from the group consisting of N, O and S, wherein R' and R" are independently selected from the group consisting of H, ($C_1$–$C_8$)alkyl and aryl. When R' and R" are attached to nitrogen, they may be combined with the nitrogen atom to form a 5-, 6-, or 7-membered ring. $R^3$, $R^4$ and $R^8$ are independently selected from the group consisting of H, halogen, CN, OH, ($C_1$–$C_8$)alkyl, heteroalkyl, aryl, heteroaryl, O($C_1$–$C_8$)alkyl, N($R^6$)($R^7$) and $OR_9$; $R^5$ is selected from the group consisting of H, ($C_1$–$C_8$)alkyl, heteroalkyl, aryl and heteroaryl; $R^6$ and $R^7$ are independently selected from the group consisting of H, ($C_1$–$C_8$) alkyl, heteroalkyl, aryl and heteroaryl; and $R^9$ is selected from the group consisting of ($C_1$–$C_8$)alkyl, heteroalkyl and haloalkyl; with the proviso that $R^2$ is not H when W is unsubstituted phenyl, X is S, Y is NH, Z is N and $R^1$ is ($C_1$–$C_8$)alkyl.

Unless otherwise indicated, the compounds provided in the above formula are meant to include pharmaceutically acceptable salts and prodrugs thereof.

One embodiment provides a compound of formula (I):

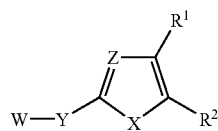

I or a pharmaceutically acceptable salt or prodrug thereof, wherein

W is selected from the group consisting of aryl, heteroaryl, ($C_1$–$C_8$)alkyl, heteroalkyl, cycloalkyl and heterocycloalkyl;

X is selected from the group consisting of $N(R^5)$, S, O, $C(R^3)=C(R^4)$, $N=C(R^4)$ and optionally, when Z is N, X can be $C(R^6)(R^7)$;

Y is selected from the group consisting of a bond, $N(R^5)$, $N(R^5)$—($C_1$–$C_8$)alkylene, O, S and $S(O)_n$, wherein the integer n is 1 or 2;

Z is selected from the group consisting of N and $C(R^8)$;

$R^1$ and $R^2$ are independently selected from the group consisting of H, halogen, CN, $CO_2R'$, CONR'R", ($C_1$–$C_8$) alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from the group consisting of N, O and S, wherein R' and R" are independently selected from the group consisting of H, ($C_1$–$C_8$)alkyl and aryl, and when R' and R" are attached to nitrogen atom, they may be combined with the nitrogen atom to form a 5-, 6-, or 7-membered ring;

$R^3$, $R^4$ and $R^8$ are independently selected from the group consisting of H, halogen, CN, OH, ($C_1$–$C_8$)alkyl, heteroalkyl, aryl, heteroaryl, O($C_1$–$C_8$)alkyl, N($R^6$)($R^7$) and $OR^9$;

$R^5$ is selected from the group consisting of H, ($C_1$–$C_8$) alkyl, heteroalkyl, aryl and heteroaryl;

$R^6$ and $R^7$ are independently selected from the group consisting of H, ($C_1$–$C_8$)alkyl, heteroalkyl, aryl and heteroaryl; and $R^9$ is selected from the group consisting of ($C_1$–$C_8$)alkyl, heteroalkyl and haloalkyl;

with the proviso that $R^2$ is not H when W is unsubstituted phenyl, X is S, Y is NH, Z is N and $R^1$ is ($C_1$–$C_8$)alkyl.

Within this embodiment is provided is a compound, wherein Z is N.

Within this embodiment is also provided a compound, wherein X is S.

Within this embodiment is also provided a compound, wherein Y is $N(R^5)$.

Within this embodiment is also provided a compound, wherein Z is N, X is S and Y is $N(R^5)$.

Within this embodiment is also provided a compound, wherein W is aryl or heteroaryl. Also provided is a compound, wherein W is aryl or heteroaryl and aryl is phenyl or naphthyl. Further provided is a compound, wherein W is aryl or heteroaryl and heteroaryl is pyridyl or quinolyl.

Within this embodiment is also provided a compound, wherein $R^1$ and $R^2$ are independently H or ($C_1$–$C_8$)alkyl.

Within this embodiment is also provided a compound, wherein $R^1$ and $R^2$ combine to form a fused 6-membered aryl or heteroaryl ring.

Within this embodiment is also provided a compound, wherein W is aryl or heteroaryl; X is S; Y is $N(R^5)$; Z is N; and $R^1$ and $R^2$ are independently H or ($C_1$–$C_8$)alkyl.

Within this embodiment is also provided a compound, wherein W is aryl or heteroaryl; X is S; Y is $N(R^5)$; Z is N; and $R^1$ and $R^2$ combine to form a fused 6-membered aryl or heteroaryl ring.

Within this embodiment is also provided a compound having the formula (II):

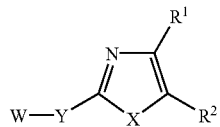

II

Within this embodiment is also provided a compound having the formula (III):

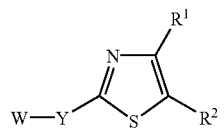

III

Within this embodiment is also provided a compound, wherein the compound is selected from the group consisting of the group consisting of:

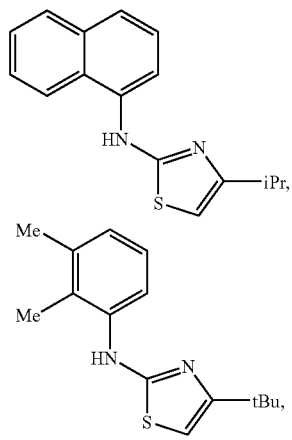

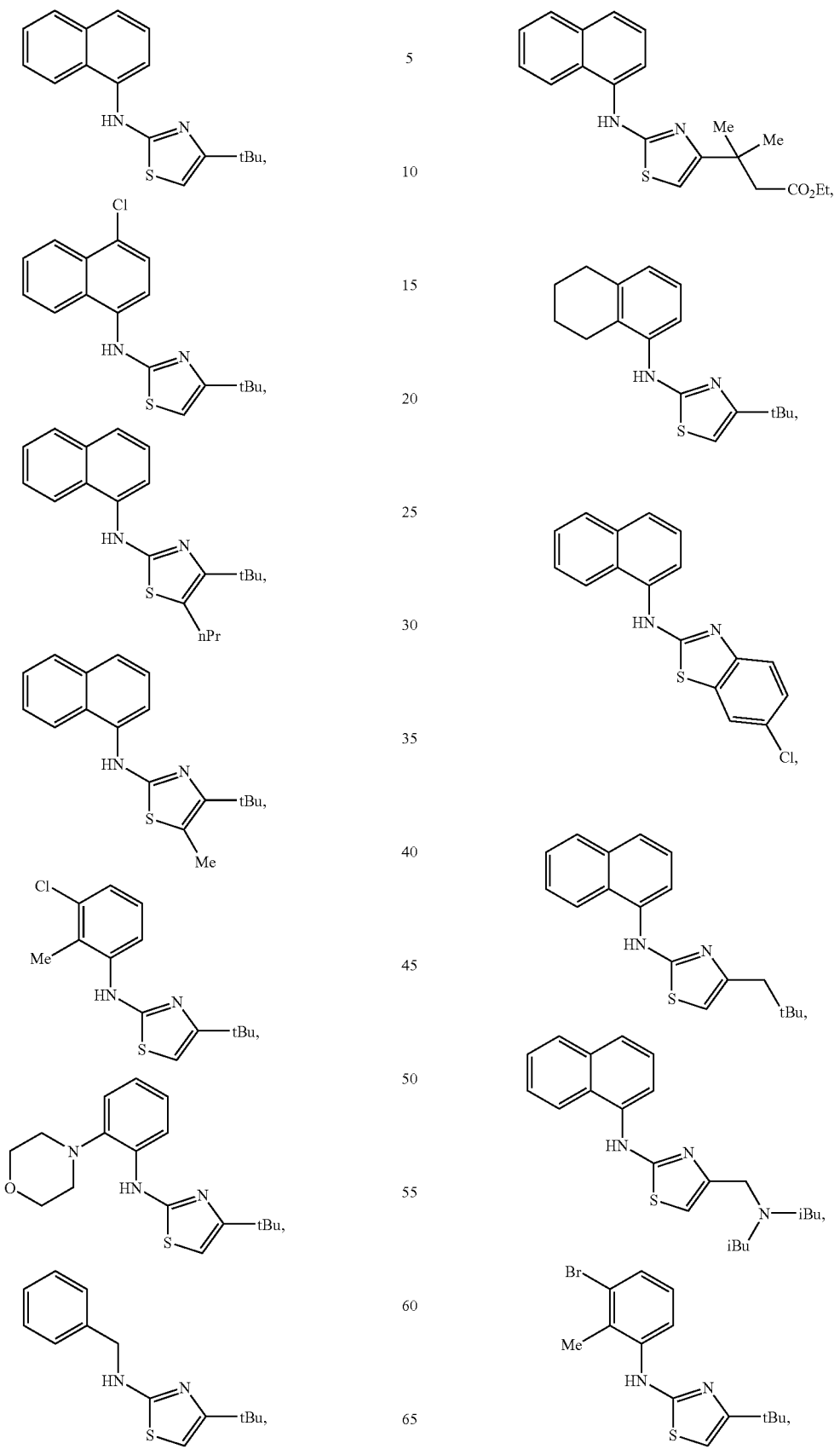

-continued
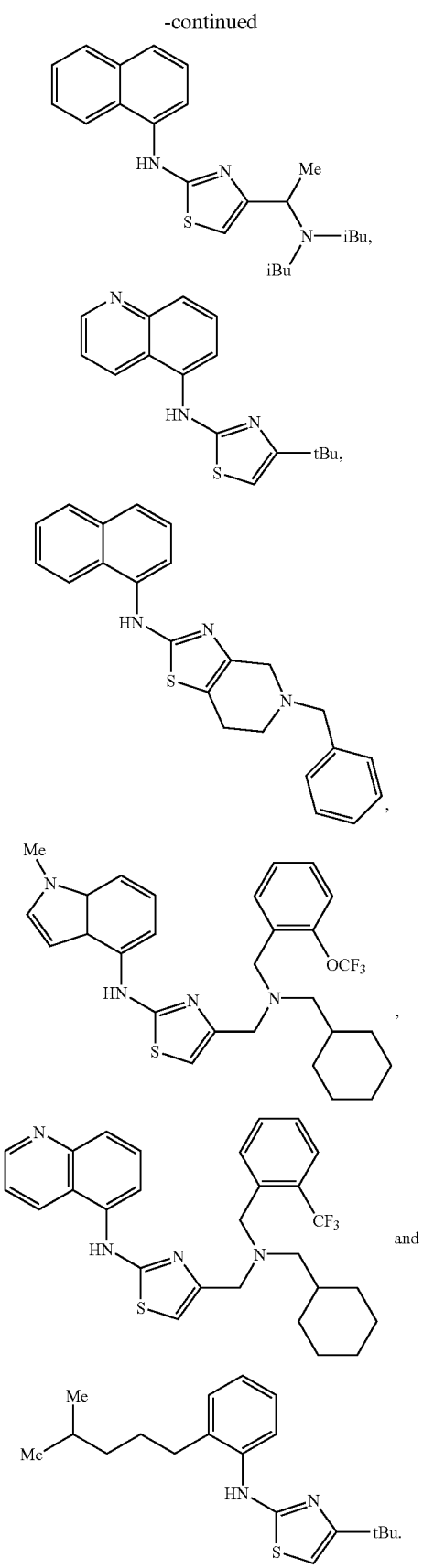
Within this embodiment is also provided a compound, wherein the compound is selected from the group consisting of the group consisting of
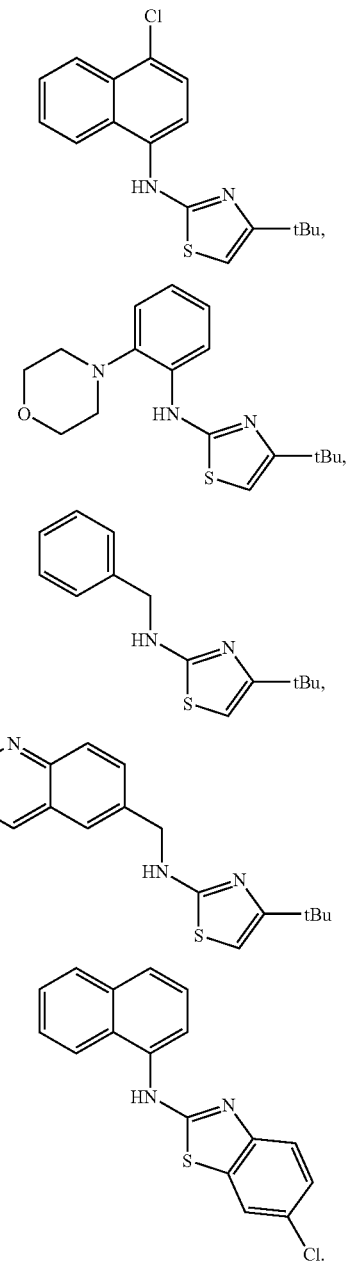
A separate embodiment provides a compound of formula (I):
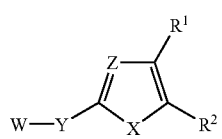

or a pharmaceutically acceptable salt or prodrug thereof, wherein

W is selected from the group consisting of substituted phenyl, substituted or unsubstituted naphthyl, pyridyl, quinolyl, $(C_1-C_8)$alkyl, heteroalkyl, cycloalkyl and heterocycloalkyl;

X is selected from the group consisting of $N(R^5)$, S, O, $C(R^3)=C(R^4)$, $N=C(R^4)$ and optionally, when Z is N, X can be $C(R^6)(R^7)$;

Y is selected from the group consisting of a bond, $N(R^5)$, $N(R^5)$—$(C_1-C_8)$alkylene, O, S and $S(O)_n$, wherein the integer n is 1 or 2;

Z is selected from the group consisting of N and $C(R^8)$;

$R^1$ and $R^2$ are independently selected from the group consisting of H, halogen, CN, $CO_2R'$, CONR'R'', $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from the group consisting of N, O and S, wherein R' and R'' are independently selected from the group consisting of H, unsubstituted $(C_1-C_8)$alkyl, unsubstituted heteroalkyl, unsubstituted aryl and aryl substituted with 1–3 halogens, alkoxy, thioalkoxy, or aryl-$(C_1-C_4)$alkyl, and when R' and R'' are attached to nitrogen atom, they may be combined with the nitrogen atom to form a 5-, 6-, or 7-membered ring;

$R^3$, $R^4$ and $R^8$ are independently selected from the group consisting of H, halogen, CN, OH, $(C_1-C_8)$alkyl, heteroalkyl, aryl, heteroaryl, $O(C_1-C_8)$alkyl, $N(R^6)(R^7)$ and $OR^9$;

$R^5$ is selected from the group consisting of H, $(C_1-C_8)$ alkyl, heteroalkyl, aryl and heteroaryl;

$R^6$ and $R^7$ are independently selected from the group consisting of H, $(C_1-C_8)$alkyl, heteroalkyl, aryl and heteroaryl; and $R^9$ is selected from the group consisting of $(C_1-C_8)$alkyl, heteroalkyl and haloalkyl.

Within this embodiment is provided a compound, wherein Z is N.

Within this embodiment is also provided a compound, wherein X is S.

Within this embodiment is also provided a compound, wherein Y is $N(R^5)$.

Within this embodiment is also provided a compound, wherein Z is N, X is S and Y is $N(R^5)$.

Within this embodiment is also provided a compound, wherein W is substituted phenyl or substituted or unsubstituted naphthyl.

Within this embodiment is also provided a compound, wherein W is pyridyl or quinolyl.

Within this embodiment is also provided a compound, wherein $R^1$ and $R^2$ are independently H or $(C_1-C_8)$alkyl.

Within this embodiment is also provided a compound, wherein $R^1$ and $R^2$ combine to form a fused 6-membered aryl or heteroaryl ring.

Within this embodiment is also provided a compound, wherein W is substituted phenyl, substituted or unsubstituted naphthyl; X is S; Y is $N(R^5)$; Z is N; and $R^1$ and $R^2$ are independently H or $(C_1-C_8)$alkyl.

Within this embodiment is also provided a compound, wherein W is substituted phenyl, substituted or unsubstituted naphthyl; X is S; Y is $N(R^5)$; Z is N; and $R^1$ and $R^2$ combine to form a fused 6-membered aryl or heteroaryl ring.

Within this embodiment is also provided a compound, wherein W is pyridyl or quinolyl; X is S; Y is $N(R^5)$; Z is N; and $R^1$ and $R^2$ are independently H or $(C_1-C_8)$alkyl.

Within this embodiment is also provided a compound, wherein W is pyridyl or quinolyl; X is S; Y is $N(R^5)$; Z is N; and $R^1$ and $R^2$ combine to form a fused 6-membered aryl or heteroaryl ring.

Yet another embodiment provides a pharmaceutical composition comprising a pharmaceutically acceptable carrier or excipient and a compound of formula (I):

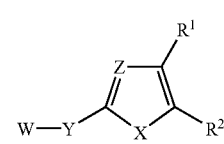

or a pharmaceutically acceptable salt or prodrug thereof, wherein

W is selected from the group consisting of aryl, heteroaryl, $(C_1-C_8)$alkyl, heteroalkyl, cycloalkyl and heterocycloalkyl;

X is selected from the group consisting of $N(R^5)$, S, O, $C(R^3)=C(R^4)$, $N=C(R^4)$, and optionally, when Z is N, X can be $C(R^6)(R^7)$;

Y is selected from the group consisting of a bond, $N(R^5)$, $N(R^5)$—$(C_1-C_8)$alkylene, O, S and $S(O)_n$, wherein the integer n is 1 or 2;

Z is selected from the group consisting of N and $C(R^8)$;

$R^1$ and $R^2$ are independently selected from the group consisting of H, halogen, CN, $CO_2R'$, CONR'R'', $(C_1-C_8)$alkyl, heteroalkyl, aryl, heteroaryl, $N(R^6)$ $R^7$), $OR^9$ and optionally, $R^1$ and $R^2$ combine to form a 5- to 8-membered ring containing from 0 to 3 heteroatoms selected from the group consisting of N, O and S, wherein R' and R'' are independently selected from the group consisting of H, unsubstituted $(C_1-C_8)$alkyl, unsubstituted heteroalkyl, unsubstituted aryl and aryl substituted with 1–3 halogens, alkoxy, thioalkoxy, or aryl-$(C_1-C_4)$alkyl. When R' and R'' are attached to nitrogen, they may be combined with the nitrogen atom to form a 5-, 6-, or 7-membered ring;

$R^3$, $R^4$ and $R^8$ are independently selected from the group consisting of H, halogen, CN, OH, $(C_1-C_8)$alkyl, heteroalkyl, aryl, heteroaryl, $O(C_1-C_8)$alkyl, $N(R^6)(R^7)$ and $OR^9$;

$R^5$ is selected from the group consisting of H, $(C_1-C_8)$ alkyl, heteroalkyl, aryl and heteroaryl;

$R^6$ and $R^7$ are independently selected from the group consisting of H, $(C_1-C_8)$alkyl, heteroalkyl, aryl and heteroaryl; and $R^9$ is selected from the group consisting of $(C_1-C^8)$alkyl, heteroalkyl and haloalkyl.

Within this embodiment is provided a pharmaceutical composition, wherein Z is N.

Within this embodiment is also provided a pharmaceutical composition, wherein X is S.

Within this embodiment is also provided a pharmaceutical composition, wherein Y is $N(R^5)$.

Within this embodiment is also provided a pharmaceutical composition, wherein Z is N, X is S and Y is $N(R^5)$.

Within this embodiment is also provided a pharmaceutical composition, wherein W is aryl or heteroaryl.

Within this embodiment is also provided a pharmaceutical composition, wherein $R^1$ and $R^2$ are independently H or $(C_1-C_8)$alkyl.

Within this embodiment is also provided a pharmaceutical composition, wherein R¹ and R² combine to form a fused 6-membered aryl or heteroaryl ring.

Within this embodiment is also provided a pharmaceutical composition, wherein W is aryl or heteroaryl; X is S; Y is N(R); Z is N; and R¹ and R² are independently H or (C₁–C₈)alkyl.

Within this embodiment is also provided a pharmaceutical composition, wherein W is aryl or heteroaryl; X is S; Y is N(R⁵); Z is N; and R¹ and R² combine to form a fused 6-membered aryl or heteroaryl ring.

Within this embodiment is also provided a pharmaceutical composition, wherein the compound has the formula (II):

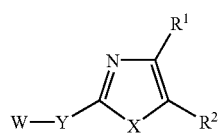

II

Within this embodiment is also provided a pharmaceutical composition, wherein the compound has the formula (III):

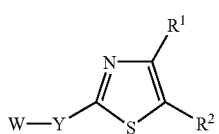

III

Within this embodiment is also provided a pharmaceutical composition, wherein the compound is selected from the group consisting of

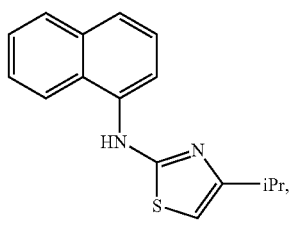

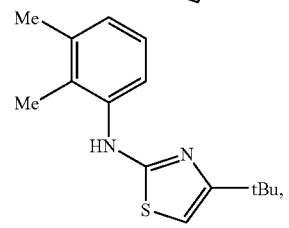

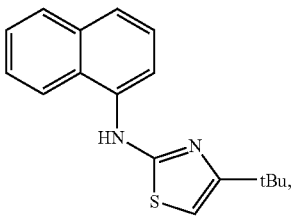

-continued

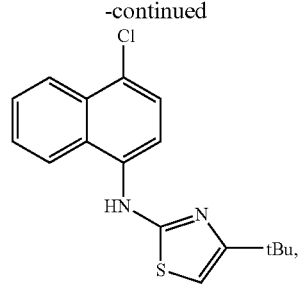

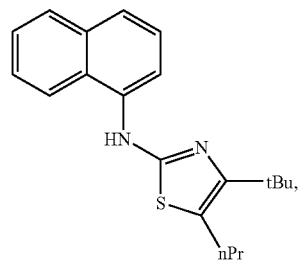

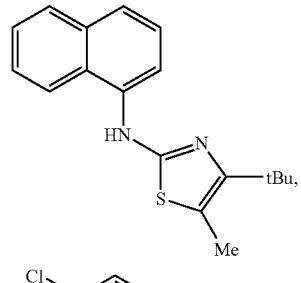

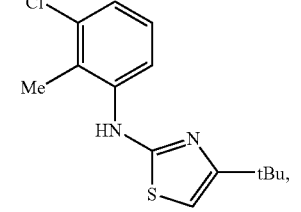

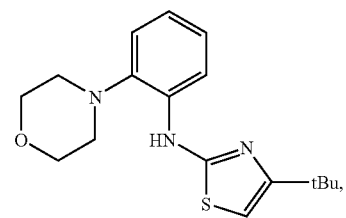

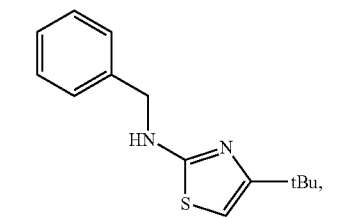

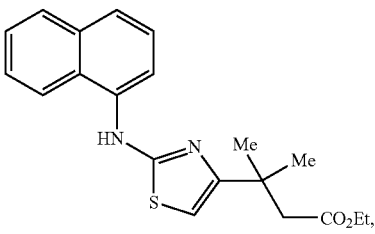

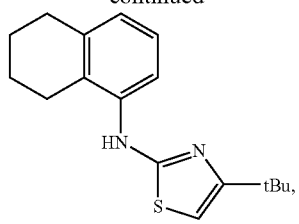
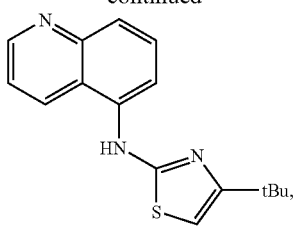
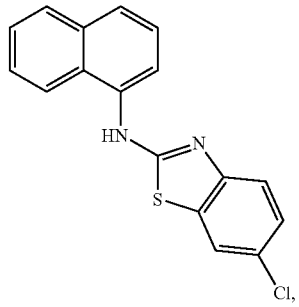
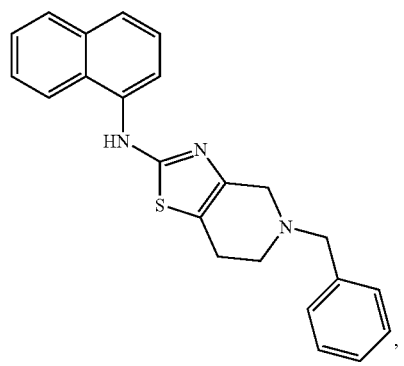
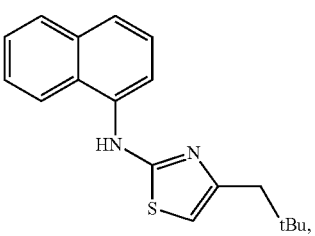
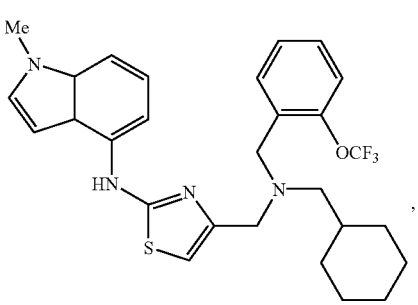
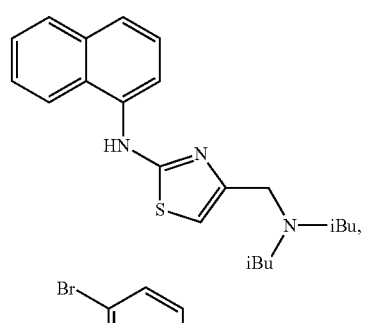
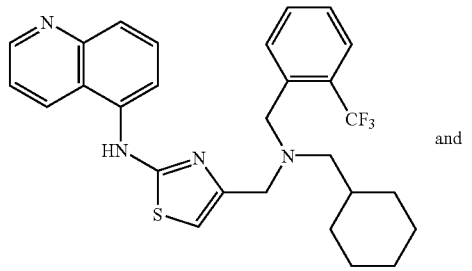
and
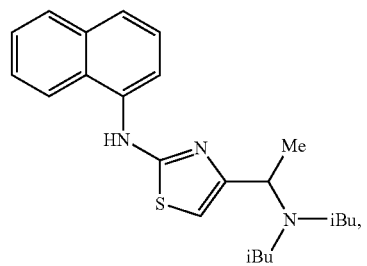
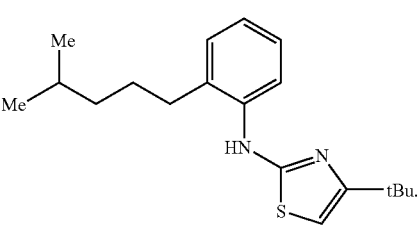

Within this embodiment is also provided a pharmaceutical composition, wherein the compound is selected from the group consisting of the group consisting of

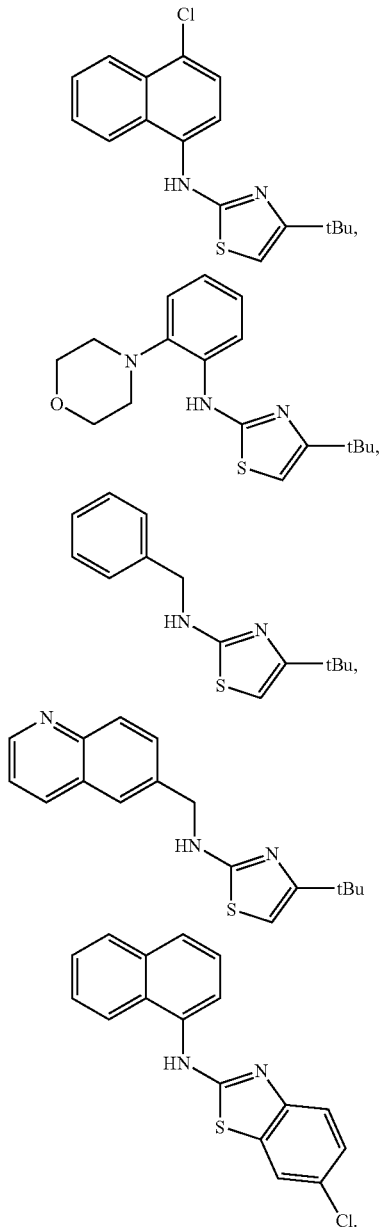

Still another embodiment provides a method of treating a CCR4-mediated condition or disease, comprising
administering to a subject in need thereof a therapeutically effective amount of a compound of formula (I):

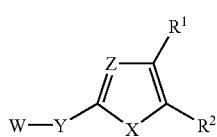

or a pharmaceutically acceptable salt or prodrug thereof, wherein

W is selected from the group consisting of aryl, heteroaryl, $(C_1-C_8)$alkyl, heteroalkyl, cycloalkyl and heterocycloalkyl;

X is selected from the group consisting of $N(R^5)$, S, O, $C(R^3)\!=\!C(R^4)$, $N\!=\!C(R^4)$ and optionally, when Z is N, X can be $C(R^6)(R^7)$;

Y is selected from the group consisting of a bond, $N(R^5)$, $N(R^5)-(C_1-C_8)$alkylene, O, S and $S(O)_n$, wherein the integer n is 1 or 2; and Z is selected from the group consisting of N and $C(R^8)$;

$R^1$ and $R^2$ are independently selected from the group consisting of H, halogen, CN, $CO_2R'$, CONR'R", $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from the group consisting of N, O and S, wherein R' and R" are independently selected from the group consisting of H, unsubstituted $(C_1-C_8)$alkyl, unsubstituted heteroalkyl, unsubstituted aryl and aryl substituted with 1–3 halogens, alkoxy, thioalkoxy, or aryl-$(C_1-C_4)$alkyl, and R' and R" are attached to nitrogen, they may be combined with the nitrogen atom to form a 5-, 6-, or 7-membered ring;

$R^3$, $R^4$ and $R^8$ are independently selected from the group consisting of H, halogen, CN, OH, $(C_1-C_8)$alkyl, heteroalkyl, aryl, heteroaryl, $O(C_1-C_8)$alkyl, $N(R^6)(R^7)$ and $OR^9$;

$R^5$ is selected from the group consisting of H, $(C_1-C_8)$alkyl, heteroalkyl, aryl and heteroaryl;

$R^6$ and $R^7$ are independently selected from the group consisting of H, $(C_1-C_8)$alkyl, heteroalkyl, aryl and heteroaryl; and $R^9$ is selected from the group consisting of $(C_1-C_8)$alkyl, heteroalkyl and haloalkyl.

Within this embodiment is provided a method, wherein Z is N.

Within this embodiment is also provided a method, wherein X is S.

Within this embodiment is also provided a method, wherein Y is $N(R^5)$.

Within this embodiment is also provided a method, wherein Z is N, X is S and Y is $N(R^5)$.

Within this embodiment is also provided a method, wherein W is aryl or heteroaryl.

Within this embodiment is also provided a method, wherein $R^1$ and $R^2$ are independently H or $(C_1-C_8)$alkyl.

Within this embodiment is also provided a method, wherein $R^1$ and $R^2$ combine to form a fused 6-membered aryl or method ring.

Within this embodiment is also provided a method, wherein W is aryl or heteroaryl; X is S; Y is $N(R^5)$; Z is N; and $R^1$ and $R^2$ are independently H or $(C_1-C_8)$alkyl.

Within this embodiment is also provided a method, wherein W is aryl or heteroaryl; X is S; Y is $N(R^5)$; Z is N; and $R^1$ and $R^2$ combine to form a fused 6-membered aryl or heteroaryl ring.

Within this embodiment is also provided a method, wherein the compound has the formula (II):
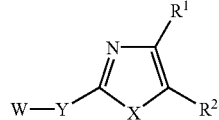
Within this embodiment is also provided a method, wherein the compound is a compound of formula (III):
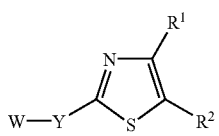
Within this embodiment is also provided a method, wherein the compound is selected from the group consisting of
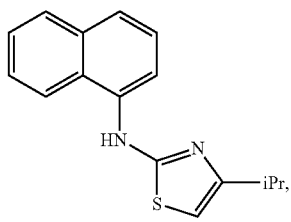
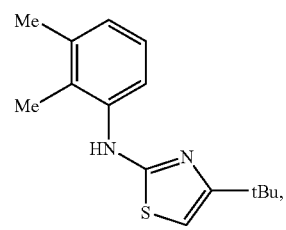
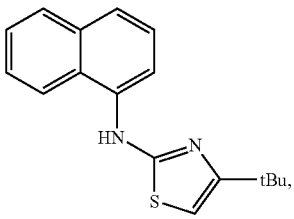
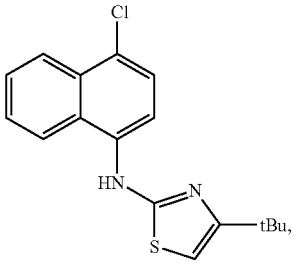
-continued
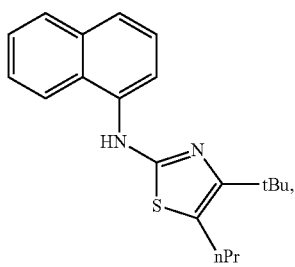
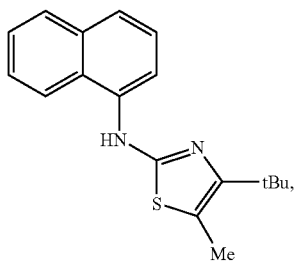
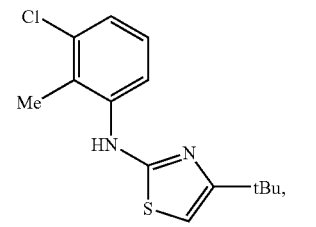
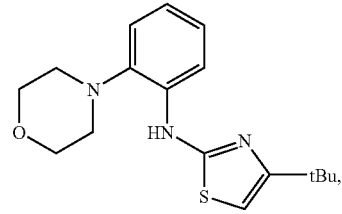
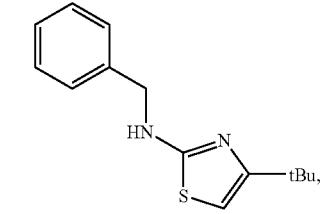
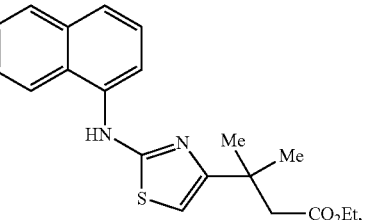
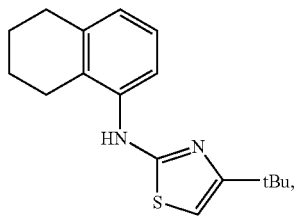

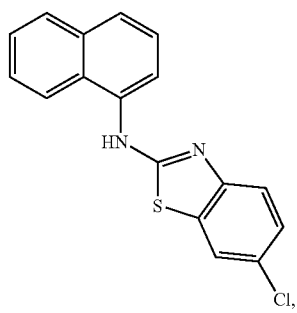
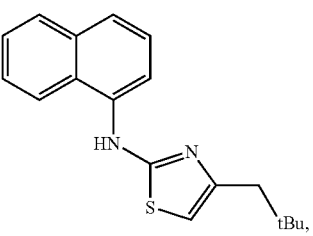
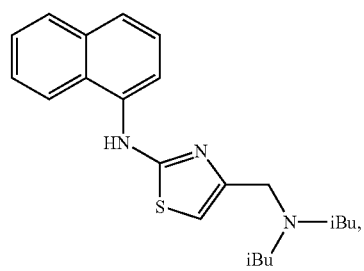
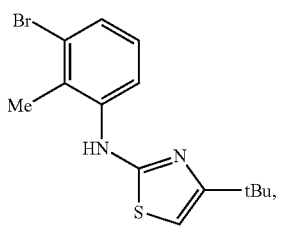
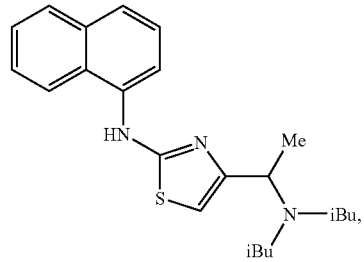
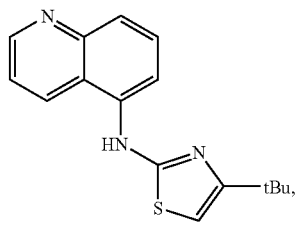
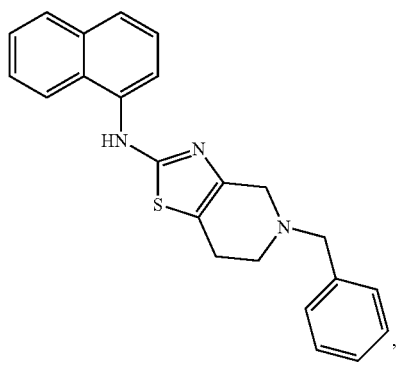
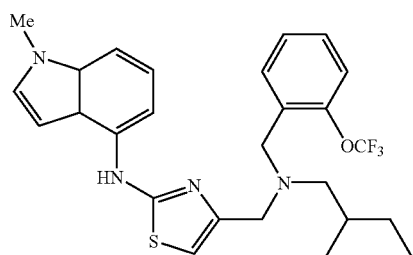
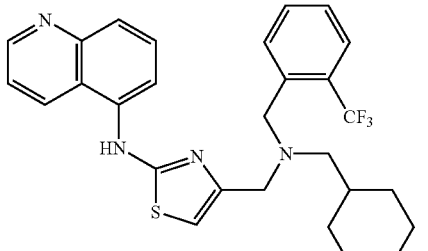
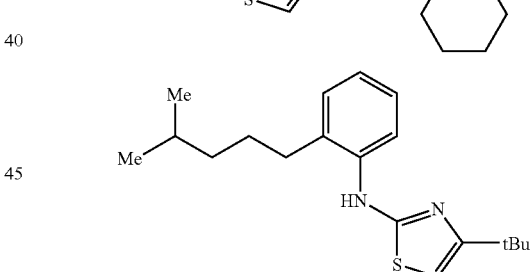
Within this embodiment is also provided a method, wherein the compound is selected from the group consisting of the group consisting of
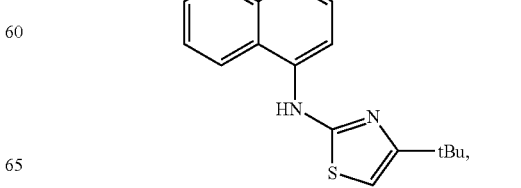

-continued

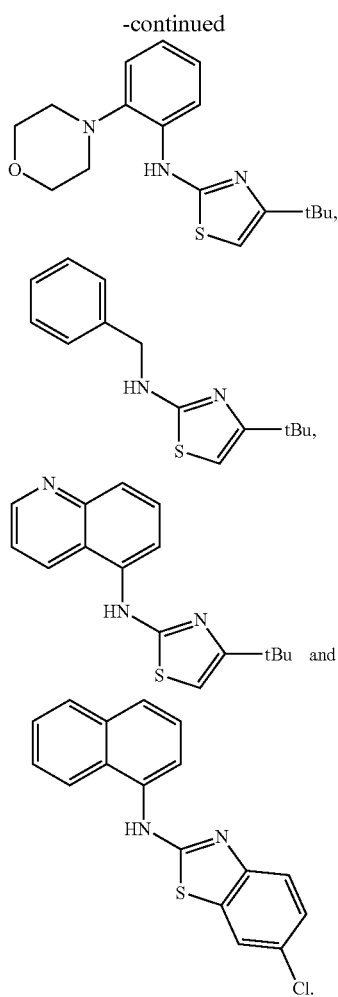

Within this embodiment is also provided a method, wherein the CCR4-mediated condition or disease is selected from the group consisting of an allergic disease, psoriasis, atopic dermatitis and asthma.

Within this embodiment is also provided a method, wherein the CCR4-mediated condition or disease is an allergic disease. Also provided is a method, wherein the CCR4-mediated condition or disease is an allergic disease and the allergic disease is selected from the group consisting of systemic anaphylaxis, hypersensitivity responses, drug allergies, insect sting allergies and food allergies.

Within this embodiment is also provided a method, wherein the CCR4-mediated condition or disease is psoriasis.

Within this embodiment is also provided a method, wherein the CCR4-mediated condition or disease is atopic dermatitis.

Within this embodiment is also provided a method, wherein the CCR4-mediated condition or disease is asthma.

Within this embodiment is also provided a method, wherein the CCR4-mediated condition or disease is an allergic condition and the compound is used alone or in combination with at least one therapeutic agent wherein the therapeutic agent is an antihistamine.

Within this embodiment is also provided a method, wherein the CCR4-mediated condition or disease is psoriasis and the compound is used alone or in combination with at least one therapeutic agent selected from the group consisting of a corticosteroid, a lubricant, a keratolytic agent, a vitamin $D_3$ derivative, PUVA and anthralin.

Within this embodiment is also provided a method, wherein the CCR4-mediated condition or disease is atopic dermatitis and the compound is used alone or in combination with at least one therapeutic agent selected from the group consisting of a lubricant and a corticosteroid.

Within this embodiment is also provided a method, wherein the CCR4-mediated condition or disease is asthma and the compound is used alone or in combination with at least one therapeutic agent selected from the group consisting of a β2-agonist and a corticosteroid.

Within this embodiment is also provided a method, wherein the compound interferes with the interaction between CCR4 and a ligand.

Within this embodiment is also provided a method, wherein the subject is a human.

Still another embodiment provides a method of modulating CCR4 function in a cell, comprising contacting the cell with a therapeutically effective amount of a compound of formula I.

Still another embodiment provides a method for modulating CCR4 function, comprising contacting a CCR4 protein with a therapeutically effective amount of a compound of formula I.

DETAILED DESCRIPTION OF THE INVENTION

Abbreviations and Definitions

Figure 1:
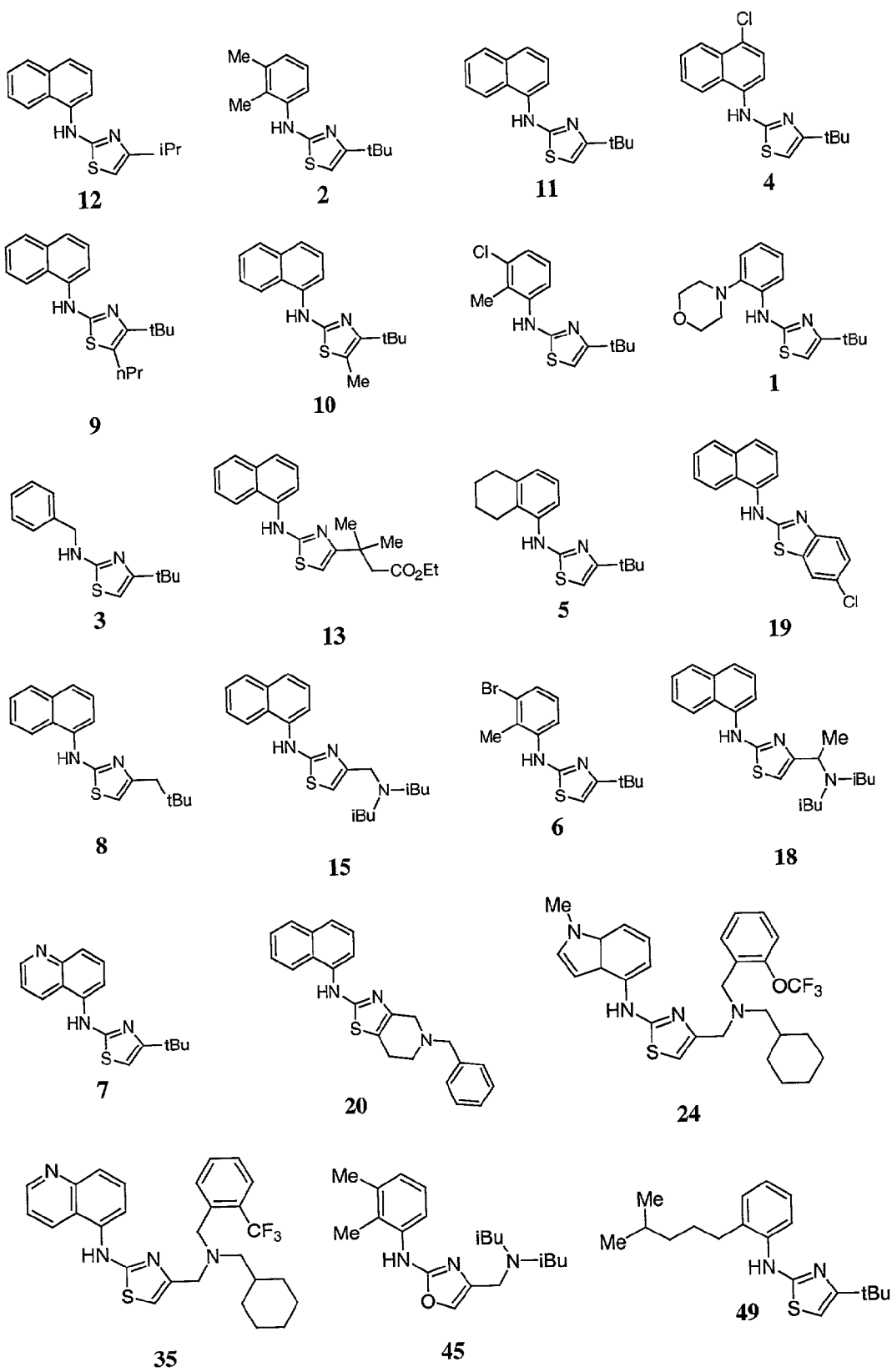
FIG. 1 provides exemplary structures of preferred compounds of the invention.

The abbreviations used herein are conventional, unless otherwise defined.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_8$ means one to eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. When a prefix such as (C$_2$–C$_8$) is used to refer to a heteroalkyl group, the number of carbons (2–8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-Cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo (C$_1$–C$_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl. Substituents for each of the above noted aryl and heteroaryl ring systems are selected from the group consisting of the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical, unless otherwise indicated. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from the group consisting of: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0–3 substituents, more preferably 0, 1, or 2 substituents, unless otherwise specified.

Similarly, substituents for the aryl and heteroaryl groups are varied and are selected from the group consisting of: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$)alkoxy, and perfluoro($C_1$–$C_4$) alkyl, in a number ranging from zero to the total number of open valences on the aromatic ring system; and where R', R" and R''' are independently selected from the group consisting of hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from the group consisting of hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

Chemokine receptors are attractive targets for the development of antiinflammatory agents. Small molecule antagonists of chemokine receptors, e.g., CC chemokine receptors, however, are not widely known. U.S. Pat. No. 6,207,665 to Hesselgesser et al. describes piperazine derivatives as CCR1 antagonists and is hereby incorporated by reference.

The present invention is directed to compounds, compositions and methods useful in the modulation of chemokine receptor function, particularly CCR4 function. Accordingly, the compounds of the present invention are compounds which inhibit at least one function or characteristic of a mammalian CCR4 protein, for example, a human CCR4 protein.

The full-length human CCR4 protein (GenBank Accession No. X85740; SWISS-PROT Accession No. P51679) has been described, see, e.g, Imai et al. (1998) *J. Biol. Chem.* 273:1764–1768, and has the sequence shown in SEQ ID NO:1.

The ability of a compound to inhibit the function of CCR4, can be demonstrated in a binding assay (e.g., ligand binding or agonist binding), a signalling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

CCR4 Antagonists

The present invention provides compounds having anti-inflammatory or anti-immunoregulatory activity. It is believed that the compounds of the invention will interfere with inappropriate T-cell trafficking by specifically modulating or inhibiting a chemokine receptor function. Chemokine receptors are integral membrane proteins which interact with an extracellular ligand, or chemokine, and mediate a cellular response to the chemokine, e.g., chemotaxis, increased intracellular calcium ion concentration. Therefore, inhibition of a chemokine receptor function, e.g., interference with a chemokine receptor-ligand interaction, will inhibit a chemokine receptor-mediated response and treat or prevent a chemokine receptor-mediated condition or disease.

While a precise understanding of the mechanism by which compounds of the present invention inhibit a chemokine receptor-mediated response is not required in order to practice the present invention, it is believed that the compounds interfere with the interaction between a chemokine receptor and one or more cognate ligands. In particular, it is believed that the compounds interfere with the interaction between CCR4 and a CCR4 ligand, e.g., TARC, MDC, etc. Compounds contemplated by the invention include, but are not limited to, the exemplary compounds provided herein.

The compounds provided herein have the general formula (I):

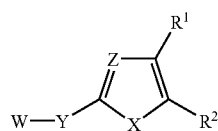

wherein W is selected from the group consisting of aryl, heteroaryl, $(C_1-C_8)$alkyl, heteroalkyl, cycloalkyl and heterocycloalkyl; X is selected from the group consisting of $N(R^5)$, S, O, $C(R^3)=C(R^4)$, $N=C(R^4)$ and optionally, when Z is N, X can be $C(R^6)(R^7)$; Y is selected from the group consisting of a bond, $N(R^5)$, $N(R^5)-(C_1-C_8)$alkylene, O, S and $S(O)_n$, wherein the integer n is 1 or 2; and Z is selected from the group consisting of N and $C(R^8)$. $R^1$ and $R^2$ are independently selected from the group consisting of H, halogen, CN, $CO_2R'$, $CONR'R''$, $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from the group consisting of N, O and S, wherein R' and R'' are independently selected from the group consisting of H, $(C_1-C_8)$alkyl and aryl. When R' and R'' are attached to nitrogen, they may be combined with the nitrogen atom to form a 5-, 6-, or 7-membered ring. $R^3$, $R^4$ and $R^8$ are independently selected from the group consisting of H, halogen, CN, OH, $(C_1-C_8)$alkyl, heteroalkyl, aryl, heteroaryl, $O(C_1-C_8)$alkyl, $N(R^6)(R^7)$ and $OR^9$; $R^5$ is selected from the group consisting of H, $(C_1-C_8)$alkyl, heteroalkyl, aryl and heteroaryl; $R^6$ and $R^7$ are independently selected from the group consisting of H, $(C_1-C_8)$alkyl, heteroalkyl, aryl and heteroaryl; and $R^9$ is selected from the group consisting of $(C_1-C_8)$alkyl, heteroalkyl and haloalkyl; with the proviso that $R^2$ is not H when W is unsubstituted phenyl, X is S, Y is NH, Z is N and $R^1$ is $(C_1-C_8)$alkyl.

Embodiments represented by formula I can be appreciated by replacing the ring system containing X and Z with an appropriate scaffold, wherein the attachment points represent the attachment of Y, $R^1$ and $R^2$ groups:

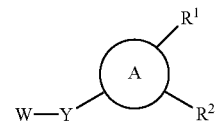

For example, the ring system or "scaffold" is meant to include the following (including substituted versions thereof) wherein the "A" ring is selected from the group consisting of the following embodiments:

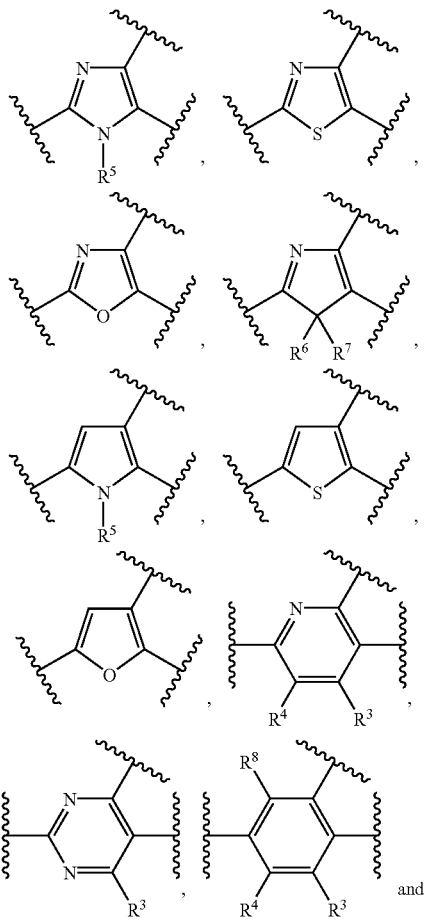

and

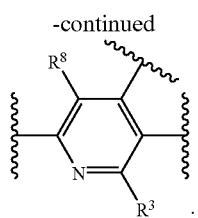

In one group of preferred embodiments Z is N. In another group, X is S. In still another group of preferred embodiments, Y is N(R$^5$). Particularly preferred are those embodiments that combine each of these preferred groups. Accordingly, in one group of particularly preferred embodiments X is S, Y is N(R$^5$) and Z is N.

In another group of preferred embodiments, W is selected from the group consisting of aryl and heteroaryl. Particularly preferred are those embodiments in which aryl is phenyl or naphthyl. Other particularly preferred embodiments are those in which heteroaryl is pyridyl or quinolyl.

In separate, but preferred embodiments, R$^1$ and R$^2$ are independently H or (C$_1$–C$_8$)alkyl.

In still other separate, but preferred embodiments, R$^1$ and R$^2$ combine to form a fused 6-membered aryl or heteroaryl ring.

In each of the above groups of preferred embodiments, R$^5$ is most preferably H.

In a particularly preferred group of embodiments, the A ring contains N and X (see formula II):

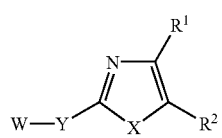

II

In formula II, W, X, Y, R$^1$ and R$^2$ have the meanings (and preferred groupings) provided above.

In another particularly preferred group of embodiments, the A ring is a thiazole ring (see formula III).

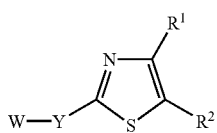

III

In formula III, W, Y, R$^1$ and R$^2$ have the meanings (and preferred groupings) provided above.

Exemplary structures within this preferred group of embodiments are shown in FIG. 1.

The vast majority of the compounds contemplated for use in the present invention are novel, while some are available from commercial sources. Unless otherwise indicated, it is to be understood that the invention includes those compounds that are novel, as well as pharmaceutical compositions, various methods (e.g., methods of treating or preventing certain CCR4-mediated conditions and diseases), and the like which include both the novel compounds of the invention and compounds that are commercially available. Exemplary commercially available compounds include: 4-(1,1-dimethylethyl)-N-phenyl-2-thiazolamine, 4-methyl-N-phenyl-2-thiazolamine, 4-(1-methylethyl)-N-phenyl-2-thiazolamine, 4-dodecyl-N-phenyl-2-thiazolamine, 2-anilino-4-isobutyl-thiazole, and 2-anilino-4-methyl-thiazole picrate.

Synthesis of CCR4 Antagonists

Synthesis routes to the compounds provided herein are described in the Examples. One of skill in the art will appreciate that the substituents (e.g., R', R", R'", etc.) can be altered before, during or after preparation of the heterocyclic scaffolding and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group.

Compositions of CCR4 Antagonists

In another aspect, the present invention provides compositions for modulating chemokine receptor function in humans and animals. The compositions comprise a compound of the present invention with a pharmaceutically acceptable carrier or excipient.

"Modulation" or "modulating" of chemokine receptor function, as used herein in its various forms, is intended to encompass antagonism, agonism, partial antagonism and/or partial agonism of a function or characteristic associated with a particular chemokine receptor, preferably the CCR4 receptor.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from the group consisting of sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouthwashes and gargles.

The pharmaceutical compositions and methods of the present invention may further comprise other therapeutically active compounds as noted herein which are usually applied in the treatment of the above mentioned pathological conditions.

Methods of Treating or Preventing CCR4-Mediated Conditions or Diseases

In yet another aspect, the present invention provides methods of treating or preventing a CCR4-mediated condition or disease by administering to a subject having such a condition or disease, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR4-mediated condition or disease" and related phrases and terms refer to a condition or disease characterized by inappropriate, e.g., less than or greater than normal, CCR4 functional activity. Inappropriate CCR4 functional activity might arise as the result of CCR4 expression in cells which normally do not express CCR4, increased CCR4 expression (leading to, e.g., inflammatory and immunoregulatory disorders and diseases) or decreased CCR4 expression. Inappropriate CCR4 functional activity might also arise as the result of TARC and/or MDC secretion by cells which normally do not secrete TARC and/or MDC, increased TARC and/or MDC expression (leading to, e.g., inflammatory and immunoregulatory disorders and diseases)

or decreased TARC and/or MDC expression. A CCR4-mediated condition or disease may be completely or partially mediated by inappropriate CCR4 functional activity. However, a CCR4-mediated condition or disease is one in which modulation of CCR4 results in some effect on the underlying condition or disease (e.g., a CCR4 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR4 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

In another group of embodiments, diseases or conditions can be treated with agonists of CCR4 function. Examples of diseases to be treated with CCR4 agonists include cancers, diseases in which angiogenesis or neovascularization play a role (neoplastic diseases, retinopathy and macular degeneration), infectious diseases (septic shock, viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

In still another group of embodiments, platelet and coagulation disorders (hereditary and acquired) can be treated with modulators of CCR4 function. Exemplary such disorders include thrombocytopenia, platelet dysfunction, hemophilia. Platelet and coagulation disorders is commonly associated with reperfusion injury, ischemia, wound healing and vascular disease.

Preferably, the present methods are directed to the treatment of diseases or conditions selected from the group consisting of allergic diseases, psoriasis, atopic dermatitis and asthma.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory conditions and diseases, including allergic diseases, psoriasis, atopic dermatitis and asthma, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with an analgesic listed above; a potentiator such as caffeine, an H2-antagonist (e.g., ranitidine), simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine.

Likewise, compounds and compositions of the present invention may be used in combination with other drugs that are used in the treatment, prevention, suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients or therapeutic agents, in addition to a compound of the present invention. Examples of other therapeutic agents that may be combined with a compound of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) soluble IL-4R (e.g., Nuvance®), IgE inhibitors, such as omalizumab (Xolair®), soluble IL-13 inhibitors and combinations thereof; (g) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (h) cyclooxygenase-2 (COX-2) inhibitors such as celecoxib (Celebrex®) and rofecoxib (Vioxx®); (i) inhibitors of phosphodiesterase type IV (PDE-IV); (j) gold compounds such as auranofin and aurothioglucose, (k) etanercept (Enbrel®), (l) antibody therapies such as orthoclone (OKT3), daclizumab (Zenapax®), basiliximab (Simulect®) and infliximab (Remicade®), (m) other antagonists of the chemokine receptors, especially CCR1, CCR2, CCR3, CCR5, CCR6, CCR8 and CCR10; (n) lubricants or emollients such as petrolatum and lanolin, (O) keratolytic agents (e.g., tazarotene), (p) vitamin $D_3$ derivatives, e.g., calcipotriene or calcipotriol (Dovonex®), (q) PUVA, (r) anthralin (Drithrocreme®), (s) etretinate (Tegison®) and isotretinoin and (t) multiple sclerosis therapeutic agents such as interferon β-1β (Betaseron®), interferon β-1α (Avonex®), azathioprine (Imurek®, Imuran®), glatiramer acetate (Capoxone®), a glucocorticoid (e.g., prednisolone) and cyclophosphamide (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In still other particularly preferred embodiments, the present methods are directed to the treatment of allergic diseases, wherein the compound of the invention is administered either alone or in combination with a second therapeutic agent, wherein said second therapeutic agent is an antihistamine. When used in combination, the practitioner can administer a combination of the therapeutic agents, or administration can be sequential.

In yet other particularly preferred embodiments, the present methods are directed to the treatment of psoriasis wherein the compound of the invention is used alone or in combination with a second therapeutic agent selected from the group consisting of a corticosteroid, a lubricant, a keratolytic agent, a vitamin $D_3$ derivative, PUVA and anthralin.

In particularly preferred embodiments, the present methods are directed to the treatment of atopic dermatitis using a compound of the invention either alone or in combination with a second therapeutic agent selected from the group consisting of a lubricant and a corticosteroid.

In particularly preferred embodiments, the present methods are directed to the treatment of asthma using a compound of the invention either alone or in combination with a second therapeutic agent selected from the group consisting of a β2-agonist and a corticosteroid.

Methods of Evaluating Putative CCR4 Modulators

In yet another aspect, the present invention includes methods to evaluate putative specific agonists or antagonists of CCR4 function. Accordingly, the present invention is directed to the use of these compounds in the preparation and execution of screening assays for compounds which modulate the function of the CCR4 chemokine receptor. For example, the compounds of this invention are useful for isolating receptor mutants, which are excellent screening tools for potent compounds. Furthermore, the compounds of this invention are useful in establishing or determining the binding site of other compounds to the CCR4 chemokine receptor, e.g., by competitive inhibition. The compounds of the instant invention are also useful for the evaluation of putative specific modulators of the CCR4 chemokine receptor, relative to other chemokine receptors including CCR1, CCR2, CCR2A, CCR2B, CCR3, CCR5, CCR6, CCR8, CCR10, CXCR3 and CXCR4. One of skill in the art will appreciate that thorough evaluation of specific agonists and antagonists of the above chemokine receptors has been hampered by the lack of availability of non-peptidyl (metabolically resistant) compounds with high binding affinity for these receptors. The compounds provided herein are particularly useful in this context.

Combinatorial libraries of putative CCR4 agonists or antagonists can be screened for pharmacological activity in in vitro or in vivo assays. Conventionally, new chemical entities with useful properties are generated by identifying a chemical compound (called a "lead compound") with some desirable property or activity, e.g., CCR4 chemokine receptor modulation activity, creating variants of the lead compound, and evaluating the properties and activities of those variant compounds. However, the current trend is to shorten the time scale for all aspects of drug discovery. Because of the ability to test large numbers of compounds quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks", such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et. al. (1994) *J. Med. Chem.* 37(9):1233–1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487–493, Houghton et. al. (1991) *Nature* 354: 84–88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909–6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217–9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al. (1994) *J. Org. Chem.* 59:658). See, generally, Gordon et al. (1994) *J. Med. Chem.* 37:1385–1401, nucleic acid libraries (see, e.g., Stratagene Corp.), peptide nucleic acid libraries (see, e.g., U.S. Pat. No. 5,539,083), antibody libraries (see, e.g., Vaughn et. al. (1996) *Nature Biotechnology* 14(3):309–314), and PCT/US96/10287), carbohydrate libraries (see, e.g., Liang et al. (1996) *Science* 274:1520–1522, and U.S. Pat. No. 5,593,853), and small organic molecule libraries (see, e.g., benzodiazepines, Baum (1993) *C&EN* January 18, page 33 and U.S. Pat. No. 5,288,514; isoprenoids, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; Asinex, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to the assays, which are typically run in parallel (e.g., in microtiter formats on microtiter plates in robotic assays). Preferred assays detect enhancement or inhibition of CCR4 receptor function.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start-up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), number of protons and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

General Procedure for Preparing Aryl Thioureas

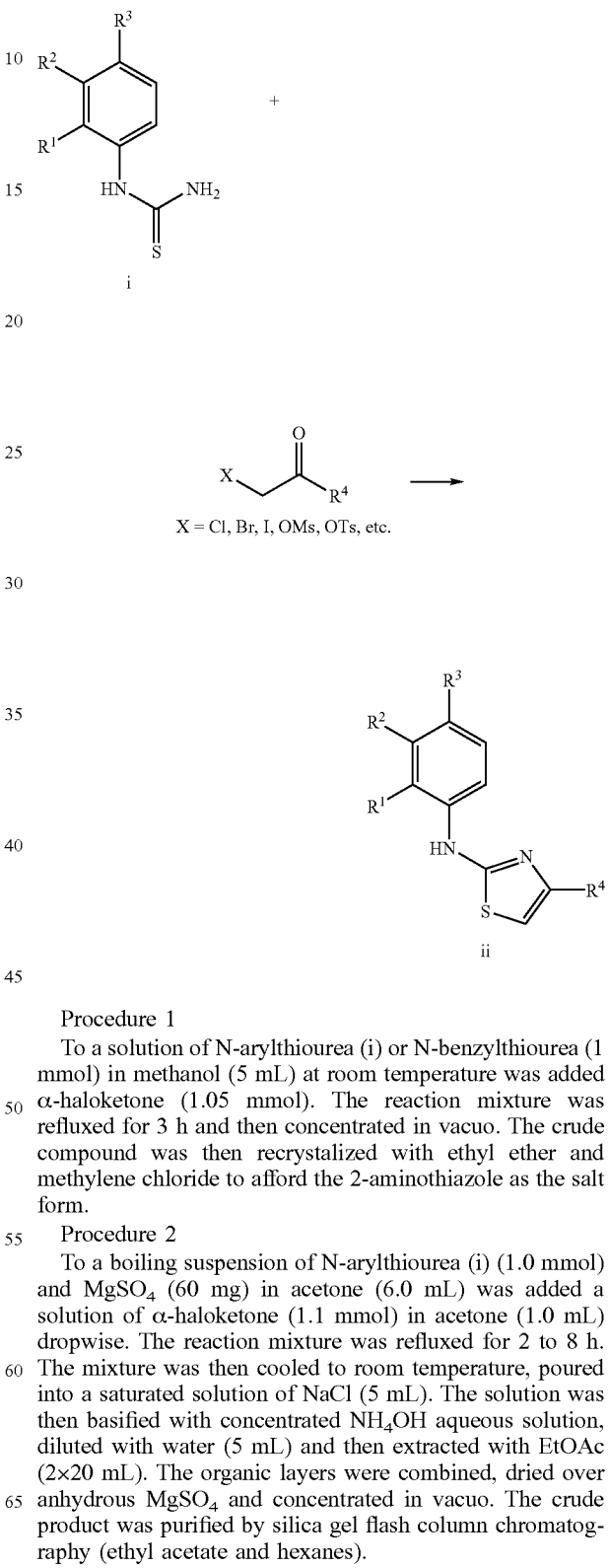

To a solution of aryl amine (4.1 mmol) in dry acetone (30 mL) at room temperature was added dropwise benzoyl-isothiocyanate (0.56 mL, 4.5 mmol). After 1 h, the reaction mixture was concentrated in vacuo to afford a solid compound, which was triturated with 50% aqueous ethanol (50 mL) to dissolve inorganic materials. The crude product was stirred with 20 mL of 10% NaOH at 98° C. for 10 min. After cooling, the basic solution was neutralized by adding 10% HCl solution. The precipitate was filtered and then washed with water.

General Procedures for Preparing 2-Amino-4-Alkyl-Substituted Thiazoles

Procedure 1

To a solution of N-arylthiourea (i) or N-benzylthiourea (1 mmol) in methanol (5 mL) at room temperature was added α-haloketone (1.05 mmol). The reaction mixture was refluxed for 3 h and then concentrated in vacuo. The crude compound was then recrystalized with ethyl ether and methylene chloride to afford the 2-aminothiazole as the salt form.

Procedure 2

To a boiling suspension of N-arylthiourea (i) (1.0 mmol) and MgSO$_4$ (60 mg) in acetone (6.0 mL) was added a solution of α-haloketone (1.1 mmol) in acetone (1.0 mL) dropwise. The reaction mixture was refluxed for 2 to 8 h. The mixture was then cooled to room temperature, poured into a saturated solution of NaCl (5 mL). The solution was then basified with concentrated NH$_4$OH aqueous solution, diluted with water (5 mL) and then extracted with EtOAc (2×20 mL). The organic layers were combined, dried over anhydrous MgSO$_4$ and concentrated in vacuo. The crude product was purified by silica gel flash column chromatography (ethyl acetate and hexanes).

In some cases, the desired thiazole products were precipitated from reaction solution. The isolation was then carried out by filtration through a Bückner funnel and washed the solid with acetone. The final products were isolated as the salt forms.

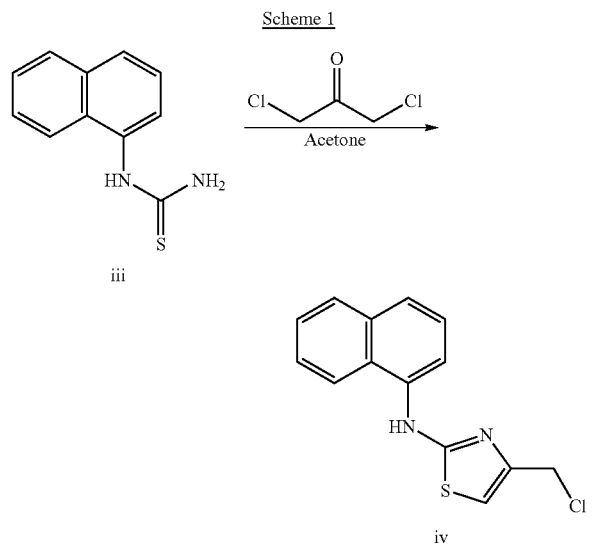

Procedure 3

(4-Chloromethyl-thiazol-2-yl)-naphthalen-1-yl-amine (iv). To a solution of naphthalen-1-yl-thiourea (iii) (2.02 g, 10 mmol) in acetone (50 mL) at room temperature was added 1,3-dichloroacetone (1.03 g, 10.5 mmol). The reaction mixture was stirred at room temperature overnight. The reaction mixture was filtered and washed with methanol. The filtrate was treated with hexane to afford a white precipitate. The precipitate was filtered and washed with hexane.

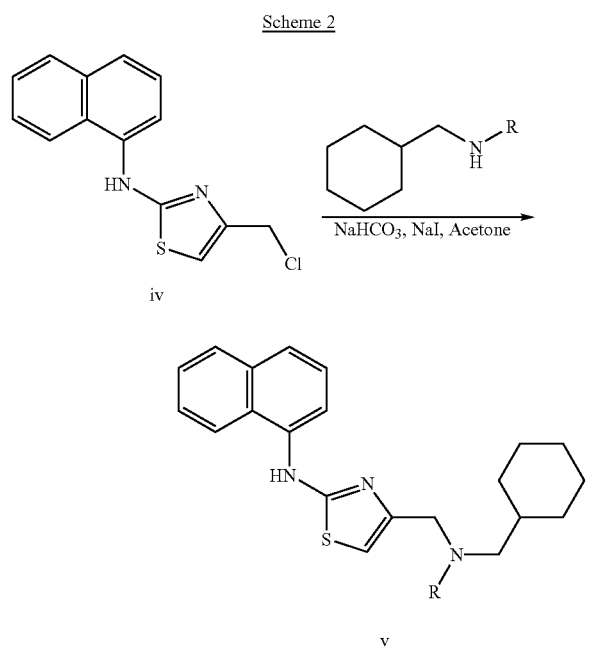

Procedure 4

To an acetone solution of (4-chloromethylthiazol-2-yl)-naphthalen-1-ylamine (iv) (0.32 g, 1 mmol) and secondary amine (1.1 mmol) at room temperature was added sodium bicarbonate (0.42 g, 5 mmol) and sodium iodide (15 mg, 0.1 mmol). The reaction mixture was heated up to reflux for 2 hours. After cooling to room temperature, the reaction mixture was quenched with water and extracted with ethyl acetate. The organic phase was dried with $MgSO_4$, filtered and concentrated in vacuo. The crude product was purified by column chromatography.

Secondary amines were prepared as outlined in Scheme 3 (below). To a solution of cyclohexanemethylamine (0.51 mL, 4.1 mmol) in 1,2-dichloroethane (30 mL) at room temperature was added aldehydes (4.1 mmol). After 15 min, the reaction mixture was cooled to 0° C. followed by the addition of sodium triacetoxyborohydride (1.13 g, 5.3 mmol) in portions then kept at room temperature overnight. The reaction mixture was quenched with water and extracted with ethyl acetate. The organic phase was dried with $MgSO_4$, filtered and concentrated in vacuo.

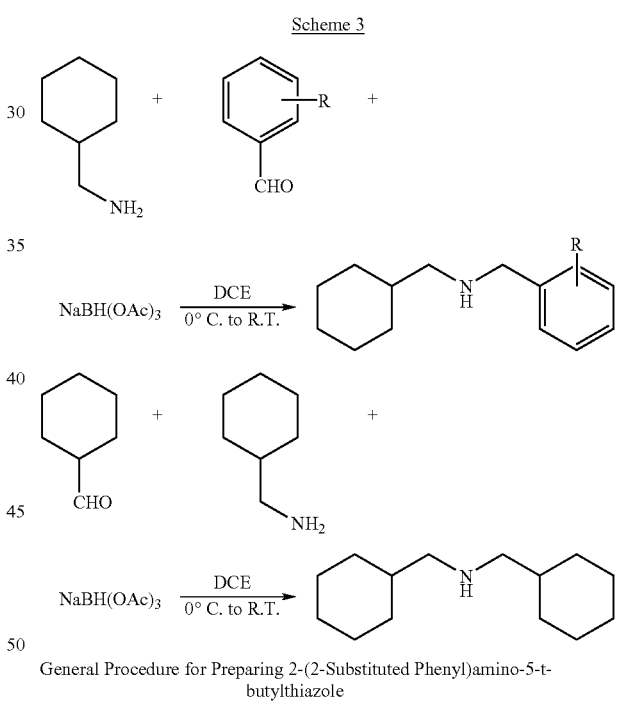

General Procedure for Preparing 2-(2-Substituted Phenyl)amino-5-t-butylthiazole

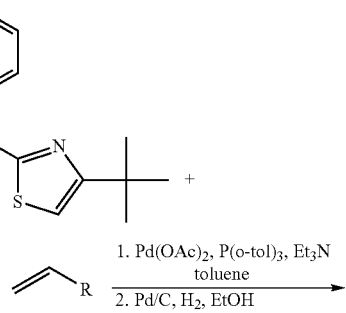

-continued

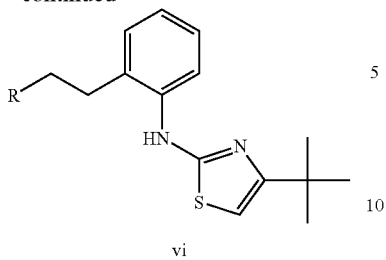

vi

To a mixture of 2-(2-bromophenyl)amino-5-t-butylthiazole (1.0 mmol), Pd(OAc)₂ (0.30 mmol), P(o-tol)₃ (0.60 mmol), and triethylamine (0.5 mmol) in 8 ml toluene, was added a monosubstituted ethylene (6.0 mmol) at room temperature. The mixture was heated in a 90° C. bath and stirred at this temperature for 2–3 hours. The reaction mixture was cooled to room temperature, diluted with EtOAc, filtered through Celite, and concentrated in vacuo. The resulting crude product was dissolved in ethanol, after which Pd on activated carbon (0.10 mmol) was added. The mixture was stirred vigorously at room temperature under an atmosphere of hydrogen for 12 h. The catalyst was removed by filtration and washed with EtOH. The filtrate was concentrated in vacuo to give a crude product, which was purified by silica gel chromatography to give the final product.

Example 1

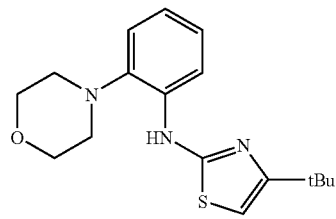

1

Compound 1 was prepared according to general procedure 1. ¹H NMR (400 MHz, CDCl₃): δ 7.4–7.5 (m, 1H), 7.3–7.4 (m, 2H), 7.2–7.3 (m, 1H), 6.17 (s, 1H), 4.04 (m, 4H), 2.96 (m, 4H), 1.47 (s, 9H). MS (ES+): 318.2 (M+H).

Example 2

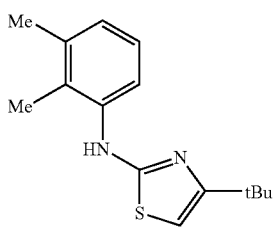

2

Compound 2 was prepared according to general procedure 1. ¹H NMR (400 MHz, CDCl₃): δ 11.2(s, br, 1H), 7.1–7.2 (m, 3H), 6.04 (s, 1H), 2.35 (s, 3H), 1.57 (s, 3H), 1.44 (s, 9H). MS (ES+): 261.1 (M+H).

Example 3

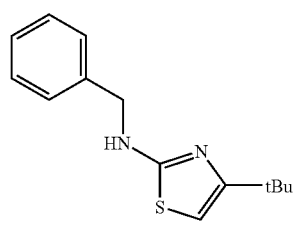

3

Compound 3 was prepared according to general procedure 1. ¹H NMR (400 MHz, CDCl₃): δ 10.1 (s, br, 1H), 7.3–7.4 (m, 5H), 6.01 (s, 1H), 4.51 (s, 2H), 1.39 (s, 9H). MS (ES+): 247.1 (M+H).

Example 4

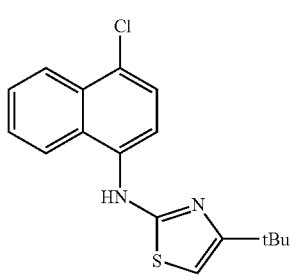

4

Compound 4 was prepared according to general procedure 1. ¹H NMR (400 MHz, CDCl₃): δ 12.0 (s, br, 1H), 8.3–8.4 (m, 2H), 7.7–7.8 (m, 2H), 7.63 (d, J=8.1 Hz, 1H), 7.53 (d, J=8.1 Hz, 1H), 6.13 (s, 1H), 1.44 (s, 9H). MS (ES+): 317.1 (M+H).

Example 5

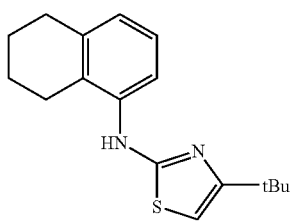

5

Compound 5 was prepared according to general procedure 1. ¹H NMR (400 MHz, CDCl₃): δ 7.1–7.2 (m, 3H), 6.14 (s, 1H), 2.82 (t, J=6 Hz, 2H), 2.77 (t, J=6 Hz, 2H), 1.8–1.9 (m, 4H), 1.41 (s, 9H). MS (ES+): 287.1 (M+H).

Example 6

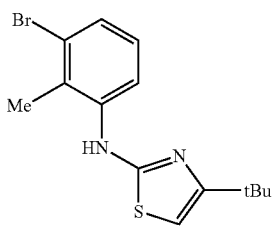

6

Compound 6 was prepared according to general procedure 1. $^1$H NMR (400 MHz, CDCl$_3$): δ 11.46 (s, br, 1H), 7.60 (d, J=8 Hz, 1H), 7.36 (d, J=8 Hz, 1H), 7.17 (t, J=8 Hz, 1H), 6.11 (s, 1H), 2.54 (s, 3H), 1.44 (s, 9H). MS (ES+): 325.1 (M+H).

Example 7

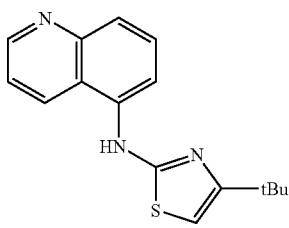

7

Compound 7 was prepared according to general procedure 1. $^1$H NMR (400 MHz, CDCl$_3$): δ 9.34 (s, br, 1H), 9.23 (d, J=8.5 Hz, 1H), 8.49 (d, J=8.1 Hz, 1H), 7.9–8.1 (m, 3H), 6.23 (s, 1H), 1.46 (s, 9H). MS (ES+): 284.1 (M+H).

Example 8

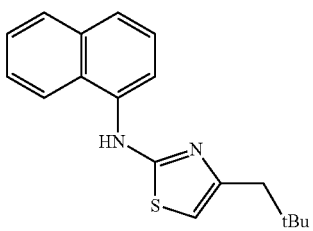

8

To a solution of 4,4-dimethyl-2-pentanone (0.25 mL, 1.7 mmol) in methanol (10 mL) was added bromine (0.09 mL, 1.7 mmol) in methanol (3 mL) dropwise at 0° C. The reaction mixture was warmed up from 0° C. to room temperature, and kept at room temperature for 1 h. 1-Naphthylthiourea (0.35 g, 1.7 mmol) was then added to the reaction mixture and refluxed for 3 h. The reaction mixture was concentrated in vacuo. The crude compound was recrystallized with ethyl ether and methylene chloride to afford the 2-aminothiazole (8) as the HBr salt. $^1$H-NMR (400 MHz, CDCl$_3$): δ 8.12 (d, J=8.1 Hz, 1H), 7.8–8.0 (m, 2H), 7.1–7.7 (m, 4H), 6.04 (s, 1H), 2.76 (s, 2H), 1.44 (s, 9H). MS (ES+): 297.2 (M+H).

Example 9

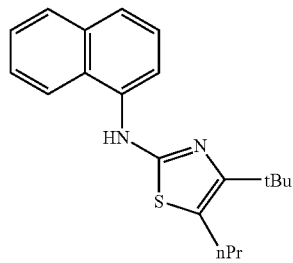

9

Compound 9 was prepared following the procedure of Example 8. $^1$H NMR (400 MHz, CDCl$_3$): δ 12.6 (s, br, 1H), 8.41 (d, J=8.1 Hz, 1H), 7.91 (dd, J=8.1, 21 Hz, 2H), 7.5–7.7 (m, 4H), 2.73 (t, J=8 Hz, 2H), 1.5–1.6 (m, 2H), 1.55 (s, 9H), 1.0 (t, J=8 Hz, 3H). MS (ES+): 325.2 (M+H).

Example 10

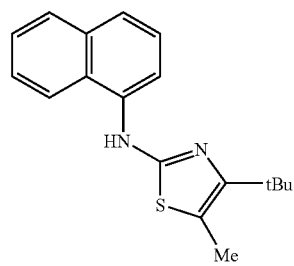

10

Compound 10 was prepared following the procedure of Example 8. $^1$H NMR (400 MHz, CDCl$_3$): δ 13.6 (s, br, 1H), 8.12 (d, J=8.1 Hz, 1H), 7.91 (dd, J=8.1, 21 Hz, 2H), 7.4–7.6 (m, 4H), 2.27 (s, 3H), 1.49 (s, 9H). MS (ES+): 297.2 (M+H).

Example 11

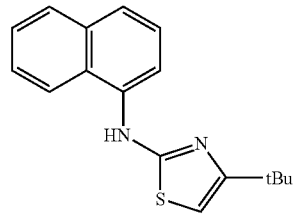

11

Compound 11 was prepared according to procedure 3. $^1$H NMR (400 MHz, CDCl$_3$): δ 11.02 (s, 1H), 8.09–8.07 (m, 1H), 7.92–7.89 (m, 1H), 7.82 (d, J=7.5 Hz, 1H), 7.69 (d, J=8.3 Hz, 1H), 7.58–7.53 (m, 2H), 7.50 (dd, J=7.8, 7.8 Hz, 1H), 6.21 (s, 1H), 1.37 (s, 9H); MS (ES+): 283.1 (M+H).

Example 12

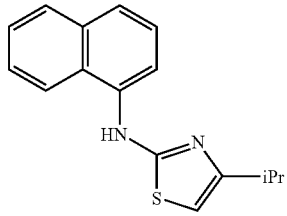

12

Compound 12 was prepared according to general procedure 3. $^1$H NMR (400 MHz, CDCl$_3$): δ 8.10 (d, J=9.4 Hz, 1H), 7.91 (dd, J=9.4, 2.7 Hz, 1H), 7.73 (d, J=7.7 Hz, 2H), 7.55–7.28 (m, 3H), 6.14 (s, 1H), 2.95 (septet, J=6.9 Hz, 1H), 6.9 (d, J=6.9 Hz, 6H); MS (ES+) 269.1 (M+H).

Example 13

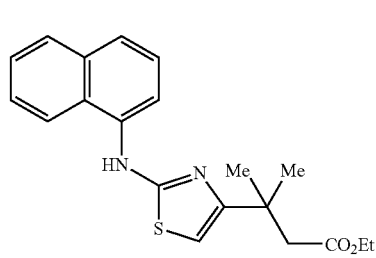

13

Compound 13 was prepared according to general procedure 3. $^1$H NMR (400 MHz, CDCl$_3$): δ 8.06 (dd, J=6.3, 3.5 Hz, 1H), 7.92–7.89 (m, 1H), 7.81 (d, J=7.5 Hz, 1H), 7.69 (d, J=8.3 Hz, 1H), 7.53 (dd, J=6.3, 3.2 Hz, 2H), 7.49 (dd, J=7.8, 7.8 Hz, 1H), 6.25 (s, 1H), 4.09 (q, J=7.1 Hz, 2H), 2.72 (s, 2H), 1.46 (s, 6H), 1.21 (t, J=7.1 Hz, 3H); MS (ES+) 355.1 (M+H).

Example 14

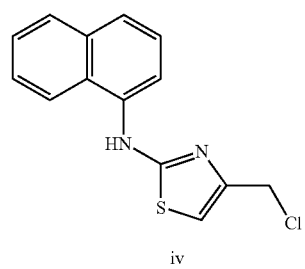

iv

-continued

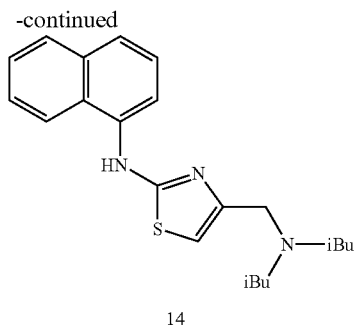

14

A mixture of compound iv (70 mg, 0.22 mmol), prepared from 1,3-dichloroacetone and N-naphthylthiourea following general procedure 3 (Scheme 1), and diisopropylamine (129 mg, 1.0 mmol) in ethanol (1.5 mL) was stirred at reflux for 6 h. After evaporating ethanol the crude product was purified by HPLC to afford the desired product (14) (TFA salt) as colorless liquid (33 mg). $^1$H-NMR (400 MHz, CDCl$_3$): δ 11.1 (s, 1H), 8.05–8.03 (m, 1H), 7.96–7.94 (m, 1H), 7.87 (d, J=8.3, 1H), 7.69 (dd, J=8.3, 0.9 Hz, 1H), 7.65–7.59 (m, 2H), 7.53 (dd, J=7.8, 7.8 Hz, 1H), 7.06 (s, 1H), 4.37 (s, 2H), 3.00 (d, J=6.7 Hz, 4H), 2.20–2.11 (m, 2H), 1.09 (d, J=6.7 Hz, 12H). MS (ES+) 368.3 (M+H).

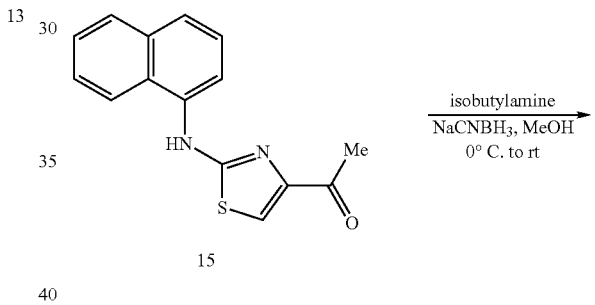

15

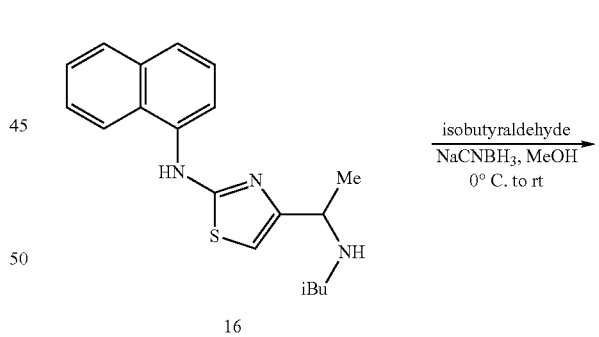

16

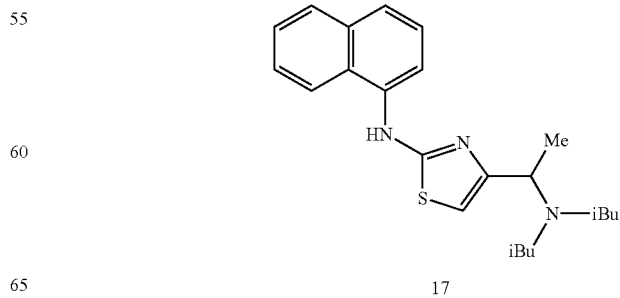

17

Example 15

4-Acetoyl-2-naphthylamino thiazole (15). The title compound was prepared from N-naphthylthiourea (606 mg, 3.0 mmol) and 1-bromo-2,3-butanedione (4.0 mmol), according to general procedure 2. This material was carried to the next step without further purification.

Example 16

4-iso-Butylamino-2'-ethyl-2-naphthylaminothiazole (16). To a stirred suspension of 4-acetoyl-2-naphthylamino thiazole (65 mg, 0.18 mmol) and iso-butylamine (53 mg, 0.72 mmol) in methanol (3 mL) was added a solution of sodium cyanoborohydride (30 mg) in methanol (1 mL) at 0° C. After stirring the mixture for 12 h, it was diluted with EtOAc (20 mL) and washed with water (2×5 mL). The organic layer was dried over MgSO4, filtered and concentrated in vacuo. The residue was purified by HPLC to give the title compound as white solid (27 mg).

Example 17

Compound 17 was prepared by reductive amination of 4-iso-butylamino-2'-ethyl-2-naphthylamino thiazole with iso-butyraldehyde, as outlined above. Purification of the crude product by HPLC afforded the desired product as a white solid (61 mg). $^1$H-NMR (400 MHz, CDCl$_3$): δ 7.97–7.95 (m, 1H), 7.83–7.81 (m, 1H), 7.68–7.62 (m, 2H), 7.47–7.45 (m, 2H), 7.39 (dd, J=7.8, 7.8 Hz, 1H), 6.64 (s, 1H), 4.53 (q, J=6.7 Hz, 1H), 2.92 (m, 2H), 2.66 (m, 2H), 1.96 (m, 2H), 1.59 (d, J=6.7 Hz, 3H), 0.94 (d, J=6.6 Hz, 6H), 0.80 (d, J=6.6 Hz, 6H). MS (ES+) 382.3 (M+H).

Example 18

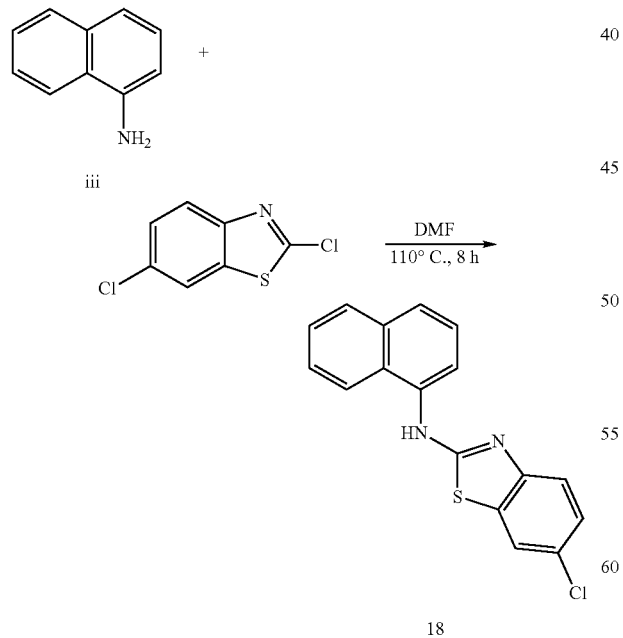

A mixture of 1-aminonaphthalene (2.0 mmol, 268 mg) and 2,6-dichlorobenzenethiazole (1.0 mmol, 203 mg) in DMF (3.0 mL) was heated at 110° C. for 8 h. The mixture was allowed to cool to room temperature, diluted with EtOAc (15.0 mL) and then extracted with H$_2$O (4×10 mL) to remove DMF. The organic layer was dried over anhydrous MgSO$_4$, filtered and concentrated in vacuo. The residue was purified by silica gel flash column chromatography (hexanes/EtOAc) to afford the desired product (18) as a yellow solid (124 mg). $^1$H-NMR (400 MHz, CDCl$_3$): δ 7.87–7.83 (m, 4H), 7.51–7.49 (m, 2H), 7.36–7.33 (m, 2H), 6.82 (dd, J=6.8, 1.5 Hz, 2H). MS (ES+) 311.0 (M+H).

Example 19

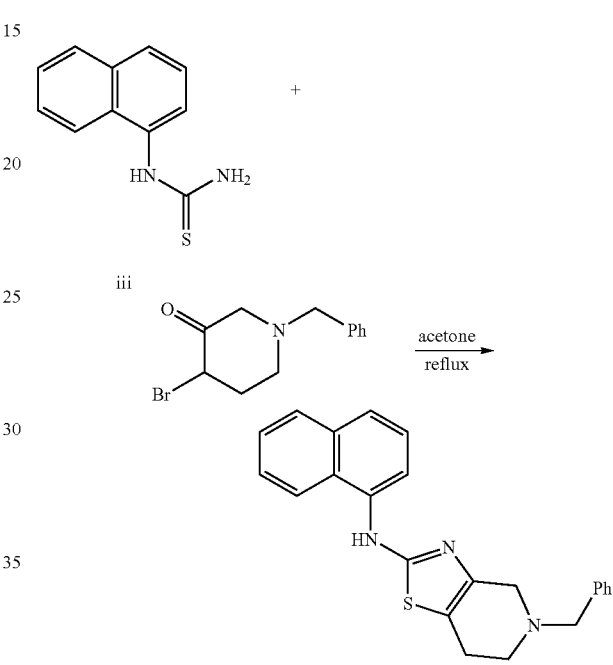

Compound 19 was prepared from 1-benzyl-3-bromo-4-piperidone (which is synthesized from 1-benzyl-4-piperidone by regioselective bromination) and N-naphthylthiourea (iii) following a general procedure. Purification of the crude product by HPLC gave compound 19 as a white solid (178 mg). $^1$H NMR (400 MHz, CDCl$_3$): δ 7.89 (d, J=9.1 Hz, 1H), 7.87 (d, J=8.4 Hz, 1H), 7.73–7.68 (m, 2H), 7.58–7.41 (m, 4H), 7.32–7.21 (m, 4H), 3.49 (s, 2H), 3.14 (s, 2H), 2.68 (t, J=5.4 Hz, 2H), 2.60 (t, J=5.4 Hz, 2H); MS (ES+) 372.2 (M+H).

Example 20

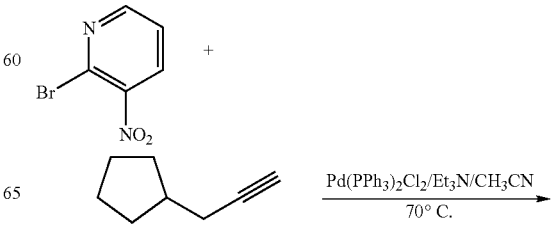

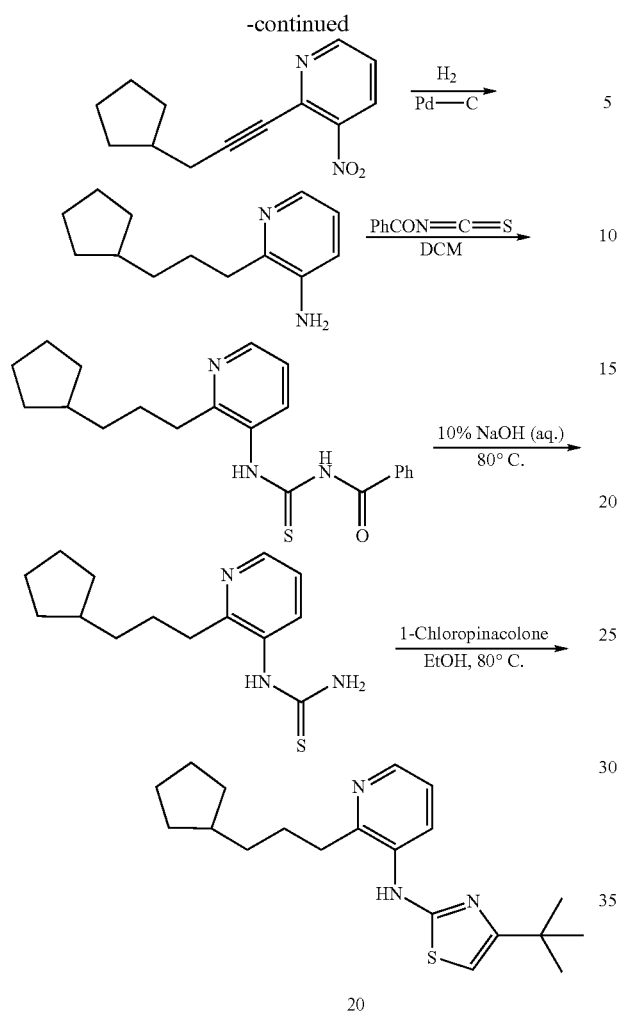
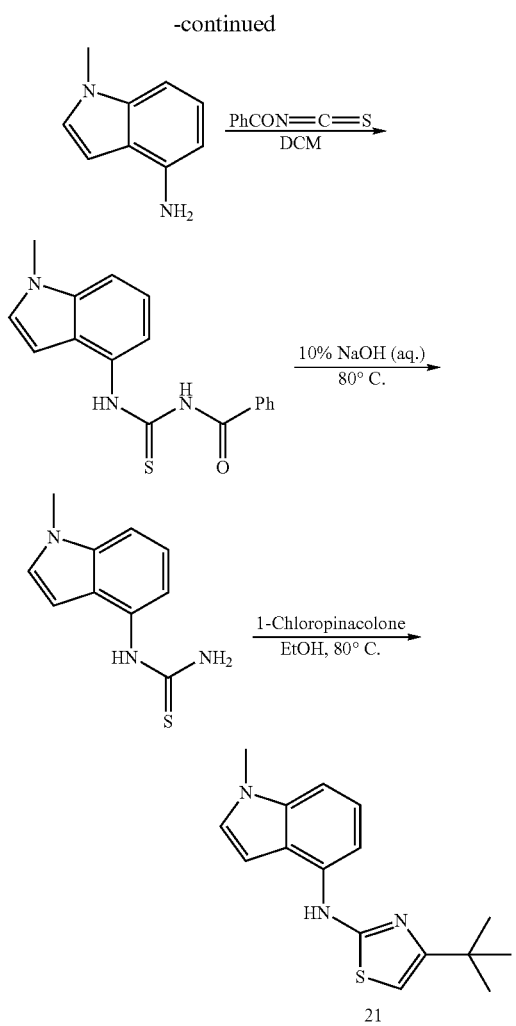

(4-tert-Butyl-thiazol-2-yl)-[2-(3-cyclopentyl-propyl)-pyridin-3-yl]-amine (20). The title compound was synthesized as a white solid, as outlined above. $^1$H NMR (DMSO-d$_6$): δ 9.30 (s, 1H), 8.39 (d, 1H, J=8.1 Hz), 8.15 (m, 1H), 7.20 (m, 1H), 6.40 (s, 1H), 2.80 (t, 2H, J=7.6 Hz), 1.63–1.70 (m, 5H), 1.45–1.53 (m, 4H), 1.31–1.35 (m, 2H), 1.23 (s, 9H), 1.02 (m, 2H). MS (ESI$^+$) 344.3 (MH$^+$).

(4-tert-Butyl-thiazol-2-yl)-(1-methyl-1H-indol-4-yl)-amine (21). The title compound was synthesized as a white solid, as outlined above. $^1$H NMR (DMSO-d$_6$): δ 9.77 (s, 1H), 7.88 (d, 1H, J=7.3 Hz), 7.22 (m, 1H, J=3.1 Hz), 7.05–7.11 (m, 2H), 6.80 (d, 1H, J=2.9 Hz), 3.77(s, 3H), 1.29(s, 9H). MS (ESI$^+$), 286.2 (MH$^+$).

Example 21

Example 22

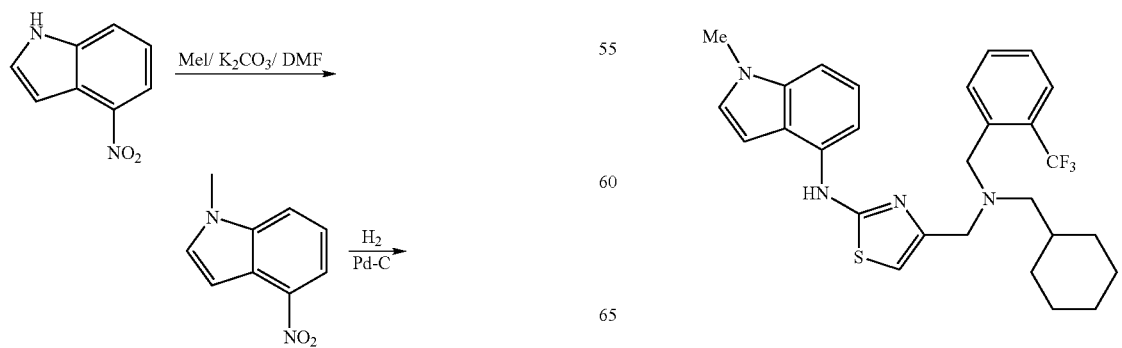

(2-{[Cyclohexylmethyl-(2-trifluoromethyl-benzyl)-amino]-methyl}-thiazol-2-yl)-(1-methyl-1H-indol-4-yl)-amine (22). The title compound was synthesized as a white solid, according to Scheme 4 (below). $^1$H NMR (DMSO-d$_6$): δ 9.82 (s, 1H), 8.04–8.08 (m, 2H), 7.67 (m, 2H), 7.44 (m, 1H), 7.23 (d, 1H, J=2.5 Hz), 7.04 (d, 2H, J=4.1 Hz), 6.80 (d, 1H, J=2.9 Hz), 6.65 (s, 1H), 3.84 (s, 2H), 3.77 (s, 3H), 3.60 (s, 2H), 2.29 (m, 2H), 1.84 (m, 2H), 1.62 (m, 4H), 1.10–1.29 (m, 3H), 0.75–0.95 (m, 2H). MS (ESI$^+$), 523.2 (MH$^+$).

Scheme 4

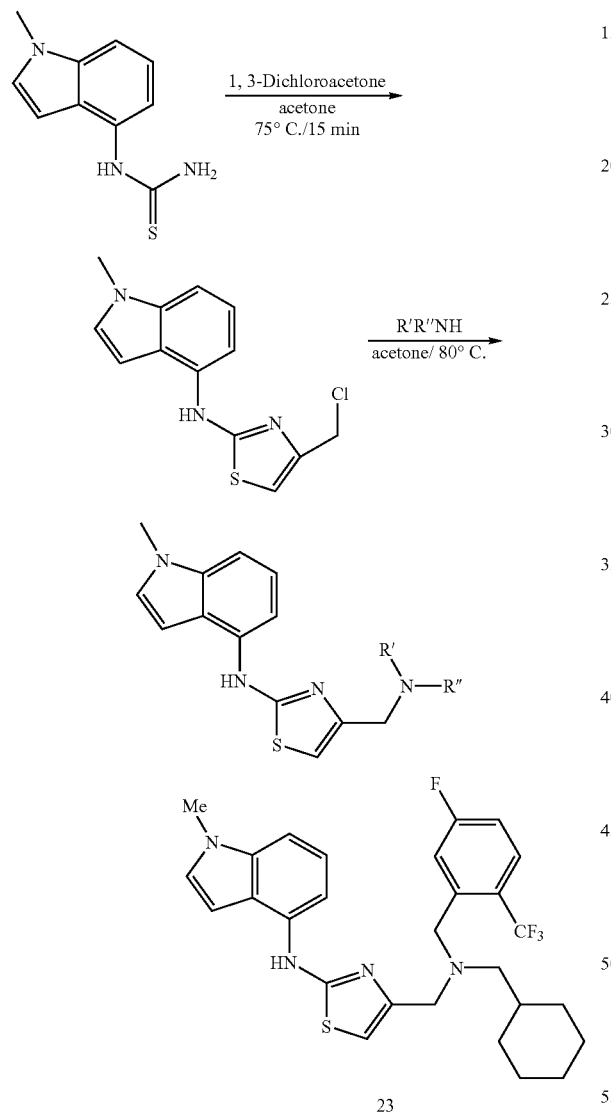

(4-{[Cyclohexylmethyl-(5-fluoro-2-trifluoromethyl-benzyl)-amino]-methyl}-thiazol-2-yl)-(1-methyl-1H-indol-4-yl)-amine (23). The title compound was synthesized as a white solid, according to Scheme 4. $^1$H NMR (DMSO-d$_6$): δ 9.82 (s, 1H), 8.07 (m, 1H), 7.87 (m, 1H), 7.76 (m, 1H), 7.26 (m, 2H), 7.05 (m, 2H), 6.82 (d, 1H, J=3.2 Hz), 6.67 (s, 1H), 3.85 (s, 2H), 3.76 (s, 3H), 3.61 (s, 2H), 2.29 (d, 2H, J=7.0 Hz), 1.91 (m, 2H), 1.58 (m, 3H), 1.10–1.29 (m, 4H), 0.72–0.80 (m, 2H). MS (ESI$^+$), 531.2 (MH$^+$).

Example 24

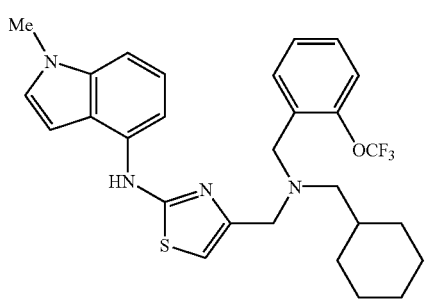

(4-{[Cyclohexylmethyl-(2-trifluoromethoxy-benzyl)-amino]-methyl}-thiazol-2-yl)-(1-methyl-1H-indol-4-yl)-amine (24). The title compound was synthesized as a white solid, according to Scheme 4. $^1$H NMR (DMSO-d$_6$): 9.82 (s, 1H), 8.00 (m, 1H), 7.79 (m, 1H), 7.30–7.40 (m, 3H), 7.22 (m, 1H), 7.05 (m, 2H), 6.81 (m, 1H), 6.63 (s, 1H). 3.76 (s, 3H), 3.71 (s, 2H), 3.55 (s, 2H), 3.80 (d, 2H, J=2.3 Hz), 1.80–1.82 (m, 2H), 1.60–1.63 9m, 3H), 1.10–1.25 (m, 4H), 0.70–0.91 (m, 2H). MS (ESI$^+$), 529.2 (MH$^+$).

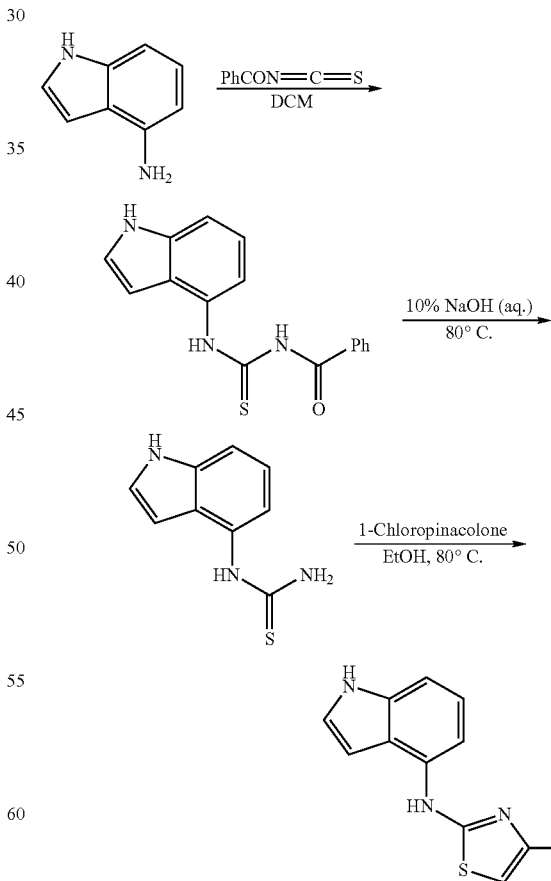

(4-tert-Butyl-thiazol-2-yl)-(1H-indol-4-yl)-amine (25). The title compound was synthesized as a white solid, as outlined above. $^1$H NMR (DMSO-d$_6$): 11.05 (s, 1H), 9.73 (s, 1H), 7.80 (m, 1H), 7.23 (s, 1H), 7.02 (m, 2H), 6.80 (s, 1H), 6.38 (d, 1H, J=1.7 Hz), 1.28 (s, 9H). MS (ESI$^+$), 272.2 (MH$^+$).

Example 26

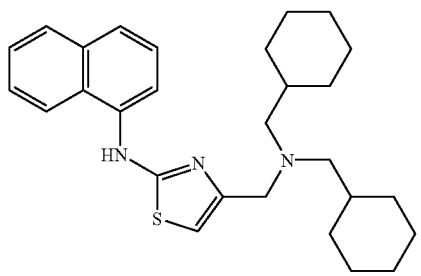

26

Compound 26 was prepared according to general procedure 4. $^1$H-NMR (400 MHz, CDCl$_3$): δ 9.96 (s, br, 1H), 8.0 (m, 3H), 7.5–7.6 (m, 3H), 7.56 (m, 1H), 7.33 (s, 1H), 4.54 (s, 2H), 3.11 (d, J=8 Hz, 4H), 1.7–1.9 (m, 12H), 1.0–1.4 (m, 10 H). MS (ES+): 448.2 (M+H).

Example 27

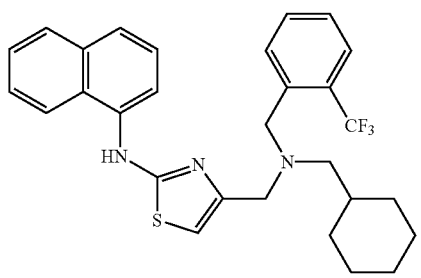

27

Compound 27 was prepared according to general procedure 4. $^1$H-NMR (400 MHz, CDCl$_3$): δ 8.05 (m, 2H), 7.91 (d, J=1 Hz, 1H), 7.80 (d, J=1 Hz, 1H), 7.73 (d, J=1 Hz, 1H), 7.62 (d, J=1 Hz, 1H), 7.5–7.6 (m, 4H), 7.32 (s, 1H), 6.46 (s, 1H), 3.77 (s, 2H), 3.50 (s, 2H), 2.27 (d, J=8 Hz, 2H), 1.5–1.9 (m, 6H), 1.1–1.3 (m, 3H), 0.8–0.9 (m, 2H). MS (ES+): 510.2 (M+H).

Example 28

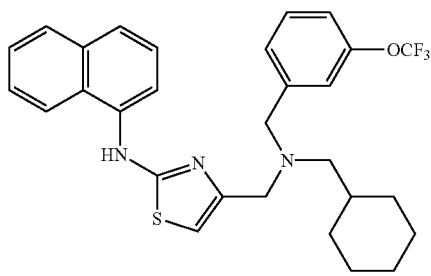

28

Compound 28 was prepared according to general procedure 4. $^1$H-NMR (400 Hz, CDCl$_3$): δ 9.58 (s, br, 1H), 8.16 (d, J=1 Hz, 1H), 7.94 (d, J=1 Hz, 1H), 7.80 (dd, J=1 Hz, 5 Hz, 2H), 7.5–7.6 (m, 3H), 7.29 (d, J=1 Hz, 1H), 7.21 (d, J=1 Hz, 1H), 7.10 (d, J=1 Hz, 1H), 6.39 (s, 1H), 3.41 (s, 2H), 3.26 (s, 2H), 2.07 (d, J=8 Hz, 2H), 0.6–1.6 (m, 1H). MS (ES+): 526.2 (M+H).

Example 29

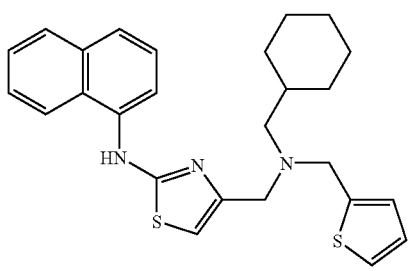

29

Compound 29 was prepared according to general procedure 4. $^1$H-NMR (400 MHz, CDCl$_3$): δ 8.0–8.1 (m, 1H), 7.9–8.0 (m, 1H), 7.76 (dd, J=4 Hz, 20 Hz, 2H), 7.5–7.6 (m, 3H), 7.22 (d, J=4.0 Hz, 1H), 6.91 (dd, J=4 Hz, 20 Hz, 2H), 6.52 (s, 1H), 3.81 (s, 2H), 3.53 (s, 2H), 2.28 (d, J=8 Hz, 2H), 0.6–1.6 (m, 11H). MS (ES+): 448.2 (M+H).

Example 30

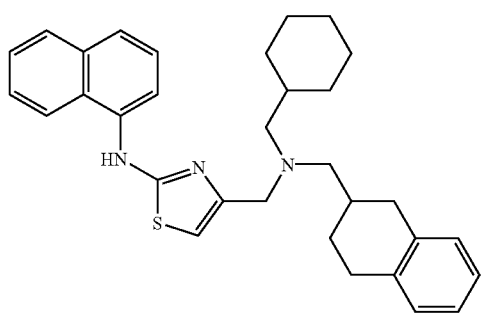

30

Compound 30 was prepared according to general procedure 4. ¹H-NMR (400 MHz, CDCl₃): δ 7.9 (dd, J=5 Hz, 5 Hz, 2H), 7.8 (d, J=6 Hz, 1H), 7.7 (d, J=6 Hz, 1H), 7.6 (d, J=5 Hz, 3H), 7.53 (d, J=6 Hz, 1H), 7.24 (t, J=6 Hz, 2H), 7.08 (d, J=6 Hz, 1H), 6.30 (s, 1H), 4.09 (t, J=6 Hz, 1H), 4.25 (dd, J=6 Hz, 20 Hz, 2H), 2.82 (t, J=6 Hz, 2H), 2.77 (t, J=6 Hz, 2H), 1.8–1.9 (m, 4H), 1.41 (s, 9H). MS (ES+): 482.3 (M+H).

Example 31

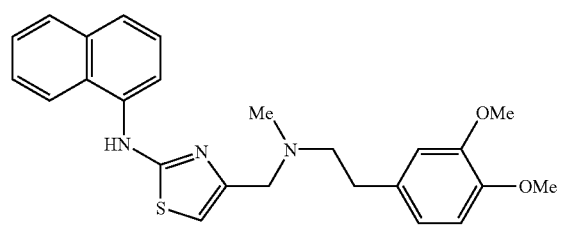

31

Compound 31 was prepared according to general procedure 4. ¹H-NMR (400 MHz, CDCl₃): δ 8.0 (t, J=8 Hz, 1H), 7.94 (t, J=8 Hz, 1H), 7.87 (d, J=8 Hz, 1H), 7.6 (m, 2H), 7.52 (t, J=8 Hz, 1H), 7.02 (s, 1H), 6.7 (m, 1H), 4.29 (s, 2H), 3.88 (s, 6H), 3.41 (t, J=8 Hz, 2H), 3.09 (t, J=8 Hz, 2H), 2.94 (s, 3H). MS (ES+): 434.2 (M+H).

Example 32

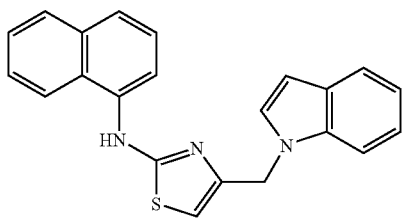

32

Compound 32 was prepared according to general procedure 4. ¹H-NMR (400 MHz, CDCl₃): δ 8.05 (m, 1H), 7.9 (m, 1H), 7.74 (dd, J=5 Hz, 10 Hz, 2H), 7.6 (m 1H), 7.51 (dd, J=5 Hz, 10 Hz, 2H), 7.12 (dd, J=5 Hz, 10 Hz, 2H), 6.72 (t, J=6 Hz, 1H), ), 6.58 (d, J=6 Hz, 1H), 6.42 (s, 1H), 4.28 (m, 2H), 3.51 (t, J=6 Hz, 1H), 3.30 (t, J=6 Hz, 1H). MS (ES+): 358.2 (M+H).

Example 33

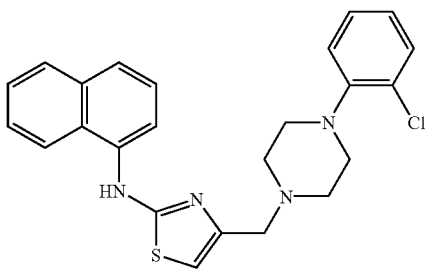

33

Compound 33 was prepared according to general procedure 4. ¹H-NMR (400 MHz, CDCl₃): δ 8.05 (d, J=1 Hz, 1H), 7.95 (d, J=1 Hz, 1H), 7.71 (dd, J=8 Hz, 1 Hz, 2H), 7.57 (dd, J=8 Hz, 1Hz, 2H), 7.51 (dd, J=8 Hz, 1Hz, 1H), 7.37 (dd, J=8 Hz, 1Hz, 1H), 7.20 (t, J=6 Hz, 1H), 7.09 (d, J=6 Hz, 1H), 6.99 (d, J=6 Hz, 1H), 6.46 (s, 1H), 3.60 (s, 2H), 3.17 (m, 5H), 2.76 (m 1H). MS (ES+): 435.2 (M+H).

Example 34

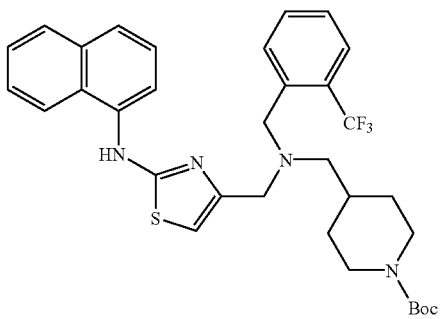

34

Compound 34 was prepared according to general procedure 4. ¹H-NMR (400 MHz, CDCl₃): δ 9.58 (s, br, 1H), 8.16 (d, J=1 Hz, 1H), 7.94 (d, J=1 Hz, 1H), 7.80 (dd, J=1 Hz, 5 Hz, 2H), 7.5–7.6 (m, 3H), 7.29 (d, J=1 Hz, 1H), 7.21 (d, J=1 Hz, 1H), 7.10 (d, J=1 Hz, 1H), 6.42 (s, 1H), 3.77 (s, 2H), 3.49 (s, 2H), 2.65 (m, 2H), 2.29 (d, J=8 Hz, 2H), 1.5–2.0 (m, 3H), 1.45 (s, 9H), 0.9–1.1 (m, 4H). MS (ES+): 610.0 (M+H).

Example 35

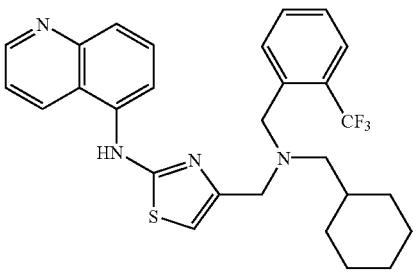

35

Compound 35 was prepared according to general procedure 4. ¹H-NMR (400 MHz, CDCl₃): δ 8.97 (dd, J=7 Hz, 1Hz, 1H), 8.41 (d, J=7 Hz, 1H), 8.05 (d, J=7 Hz, 1H), 7.98 (d, J=7 Hz, 1H), 7.84 (d, J=7 Hz, 1H), 7.75 (dd, J=7 Hz, 1 Hz, 1H), 7.62 (t, J=7 Hz, 1H), 7.43 (dd, J=7 Hz, 1Hz, 1H), 7.32 (t, J=7 Hz, 1H), 6.49 (s, 1H), 3.78 (s, 2H), 3.52 (s, 2H), 2.30 (d, J=8 Hz, 2H), 0.6–1.6 (m, 11H). MS (ES+): 511.2 (M+H).

Example 36

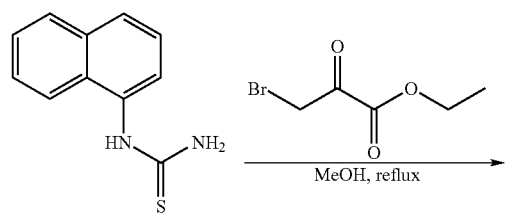

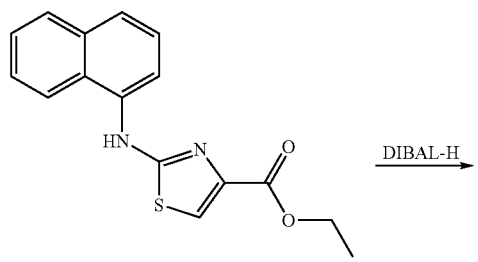

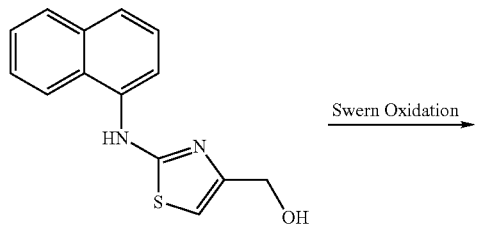

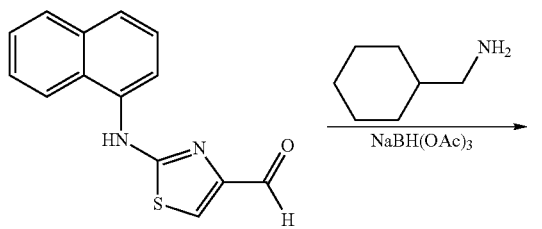

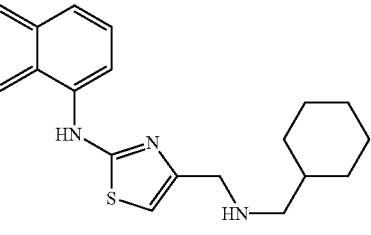

36

4-[(Cyclohexylmethylamino)-methyl]-thiazol-2-yl-naphthalen-1-yl-amine (36). The title compound was prepared as outlined above.

Example 37

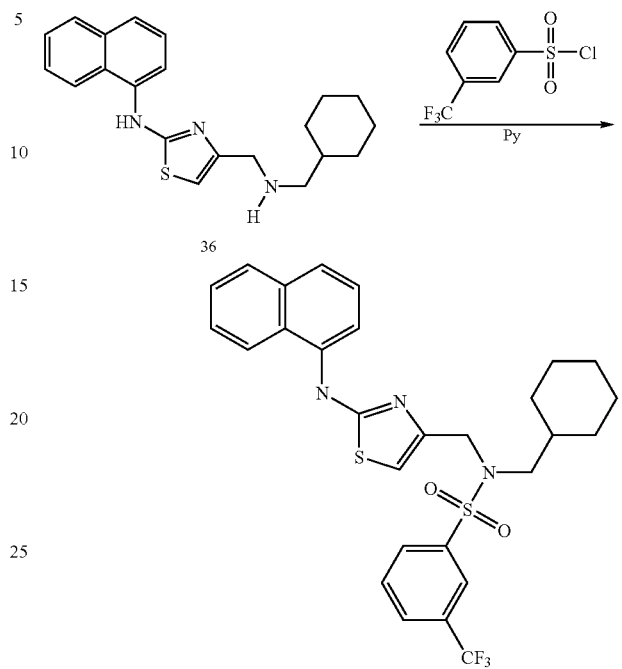

Compound 37 was synthesized as a white solid. H-NMR (400 MHz, CDCl₃): δ 8.10 (s, 1H), 7.8–8.0 (m, 4H), 7.7 (t, J=5 Hz, 2H), 7.5–7.6 (m, 4H), 6.39 (s, 1H), 4.39 (s, 2H), 3.21 (d, J=7 Hz, 2H), 1.6–2.0 (m, 6H), 1.2–1.4 (m, 3H), 0.9–1.0 (m, 2H). MS (ES+): 560.2 (M+H).

Example 38

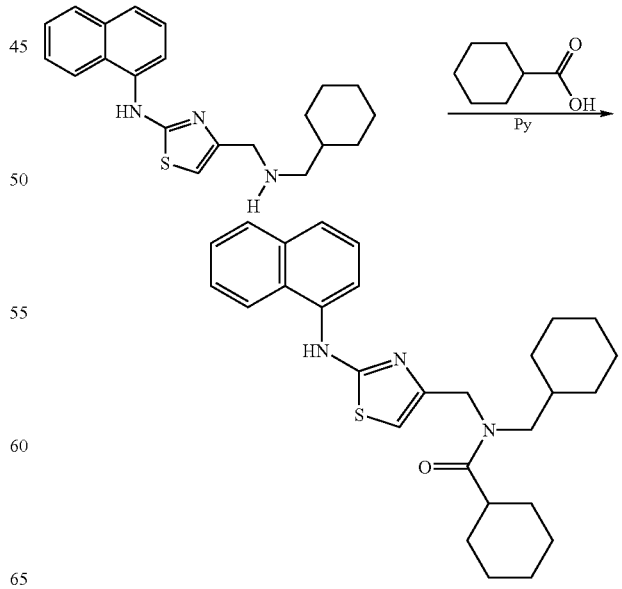

Compound 38. ¹H-NMR (400 MHz, CDCl₃): δ 8.10 (m, 1H), 7.95 (m, 1H), 7.5–7.6 (m, 2H), 7.3–7.4 (m, 3H), 6.12 (s, 1H), 4.23 (s, 2H), 3.18 (d, J=7 Hz, 2H), 1.6–2.0 (m, 14H), 1.2–1.4 (m, 5H), 0.9–1.0 (m, 3H). MS (ES+): 462.3 (M+H).

Example 39

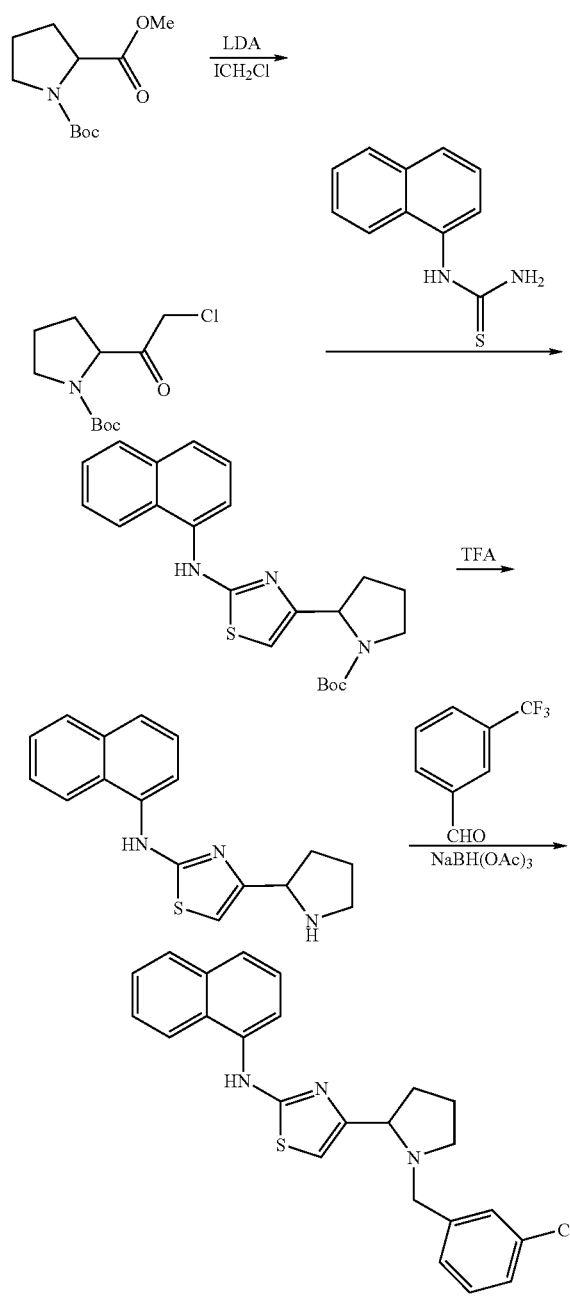

Compound 39 was prepared as outlined above. ¹H-NMR (400 MHz, CDCl₃): δ 8.07 (d, J=7 Hz, 1H), 7.96 (d, J=7 Hz, 1H), 7.85 (d, J=7 Hz, 1H), 7.69 (d, J=7 Hz, 1H), 6.7–7.7 (m, 9H), 6.88 (s, 1H), 4.0–4.3 (m, 3H), 3.65 (s, 1H), 2.2–2.5 (m, 5H). MS (ES+): 454.0 (M+H).

Example 40

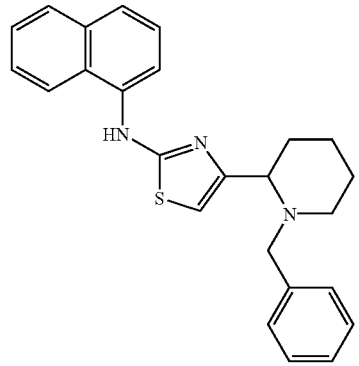

¹H-NMR (400 MHz, CDCl₃): δ 8.07 (d, J=7 Hz, 1H), 7.76 (d, J=7 Hz, 1H), 7.72 (m, 2H), 7.5 (m, 4H), 7.1–7.3 (m, 4H), 6.51 (s, 1H), 5.46 (t, J=7 Hz, 1H), 3.91 (s, 2H), 2.8 (m, 2H), 1.8 (m, 2H), 1.3 (m, 2H). MS (ES+): 297.2 (M+H).

Example 42

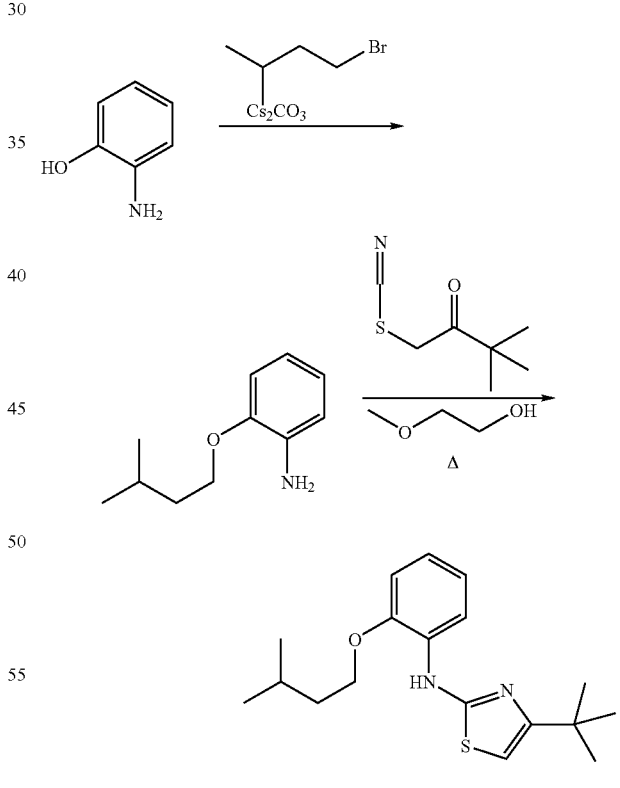

(4-tert-Butyl-thiazol-2-yl)-[2-(3-methyl-butoxy)-phenyl]-amine (42). ¹H NMR (400 MHz) (CDCl₃) δ 8.00 (d, 1H); 7.63 (bs, 1H); 6.96–6.85 (m, 3H); 6.19 (s, 1H); 4.05 (t, 2H); 1.84–1.72 (m, 3H); 1.31 (s, 9H); 0.96 (d, 6H). MS ESI m/e: 319.2 (M+H).

Example 43
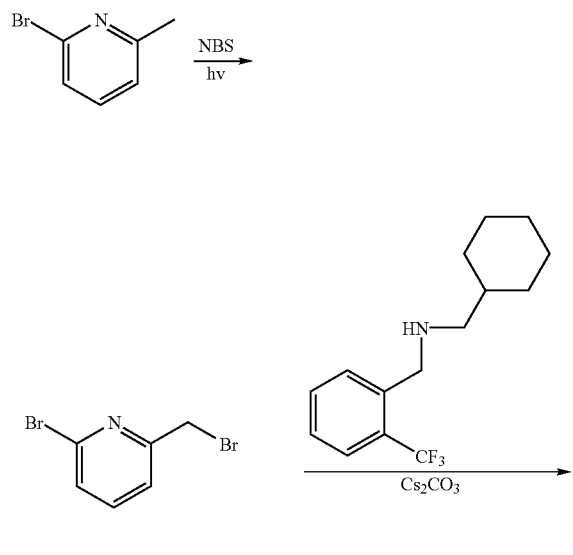
Example 44
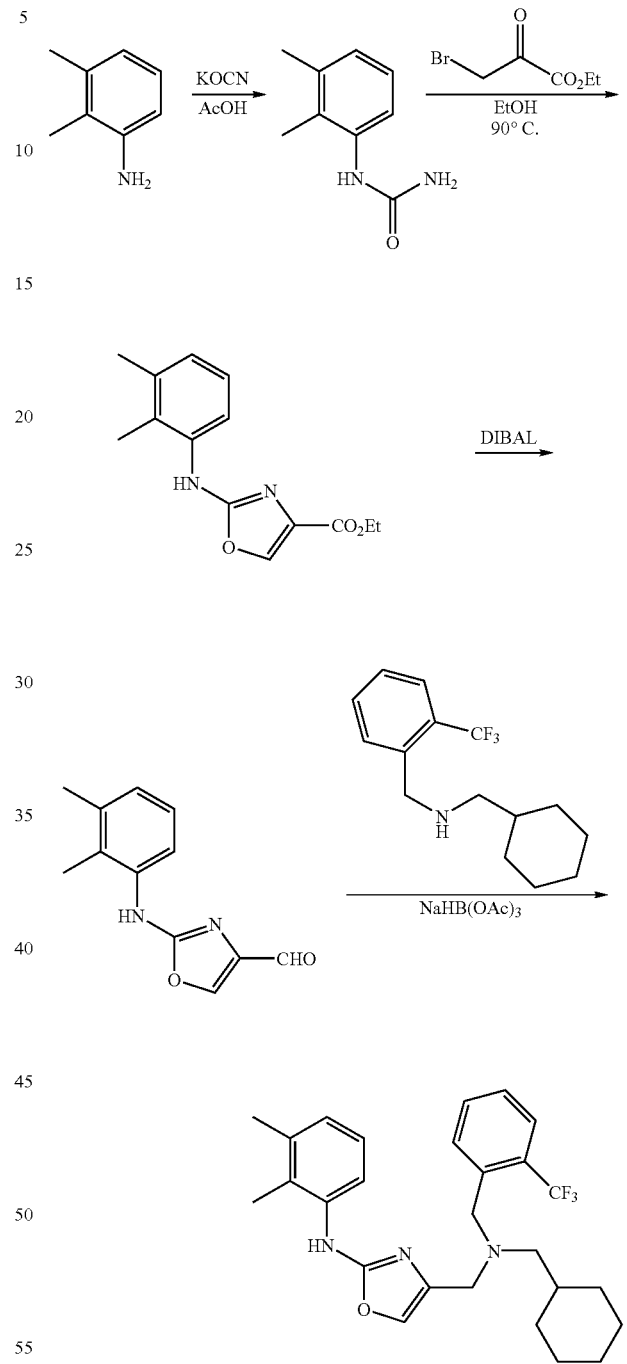
(6-{[Cyclohexylmethyl-(2-trifluoromethyl-benzyl)-amino]-methyl}-pyridin-2-yl)-(2,3-dimethyl-phenyl)-amine (43). $^1$H NMR (400 MHz) (CDCl$_3$) δ 8.05 (d, 1H); 7.60 (d, 1H); 7.53 (t, 1H); 7.41 (t, 1H); 7.29 (t, 1H); 7.22 (d, 1H); 7.09 (t, 1H); 6.99 (t, 2H); 6.36 (d, 2H); 6.31 (bs, 1H); 3.78 (s, 2H); 3.59 (s, 2H); 2.32–2.29 (m, 5H); 2.18 (s, 3H); 1.88 (d, 2H); 1.70–1.56 (m, 4H); 1.26–1.09 (m, 4H); 0.87–0.81 (m, 2H).
(4-{[Cyclohexylmethyl-(2-trifluoromethyl-benzyl)-amino]-methyl}-oxazol-2-yl)-(2,3-dimethyl-phenyl)-amine (44). $^1$H NMR (400 MHz) (d$_6$-acetone) δ 8.10 (d, 1H); 7.98 (bs, 1H); 7.89 (d, 1H); 7.63 (d, 1H); 7.59 (t, 1H); 7.36 (t, 1H); 7.31 (s, 1H); 7.04 (t, 1H); 6.86 (d, 1H); 3.85 (s, 2H); 3.48 (s, 2H); 2.32 (d, 2H); 2.26 (s, 3H); 2.22 (s, 3H); 1.85 (d, 2H); 1.65–1.59 (m, 4H); 1.25–1.08 (m., 4H); 0.85–0.73 (m, 2H). MS ESI m/e: 472.2 (M+H).

Example 45

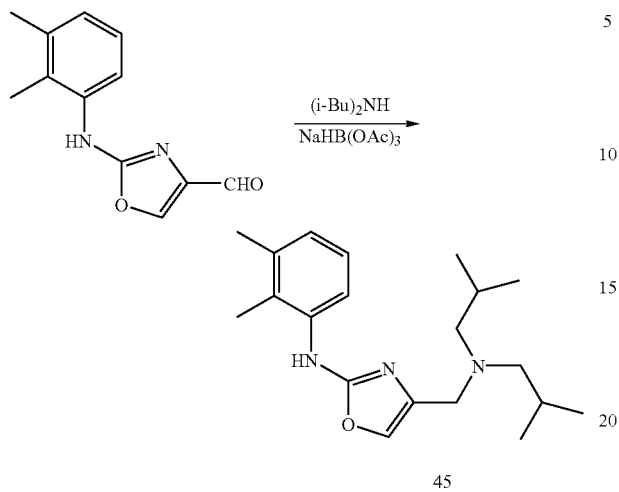

{4-[(Diisobutylamino)-methyl]-oxazol-2-yl}-(2,3-dimethyl-phenyl)-amine (45). ¹H NMR (400 MHz) (CDCl₃) δ 7.11–6.59 (m, 3H); 5.30 (s, 1H); 3.79 (s, 2H); 2.36 (s, 3H); 2.29 (s, 3H); 2.26 (d, 4H); 2.11 (m, 2H); 1.01 (s, 12H).

Example 49

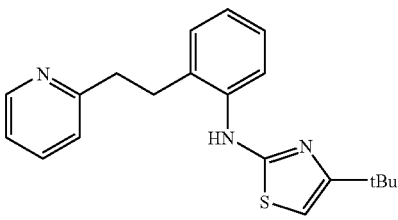

Compound 49 was prepared according to the general procedure for preparing 2-(2-substituted phenyl)amino-5-t-butylthiazoles (vi). ¹H-NMR (400 MHz, CDCl₃): δ 7.65 (d, 1H), 7.23–7.29 (m, 2H), 7.09–7.13 (m, 1H), 6.17 (s, 1H), 2.61–2.65(m, 2H), 1.61–1.64 (m, 1H), 1.56–1.60 (m, 2H), 1.26–1.30 (m, 2H), 0.87–0.89 (m, 6H), 1.33 (s, 9H). MS (ESI⁺): 317.2 (M+H).

Example 50

Compound 50 was prepared according to the general procedure for preparing 2-(2-substituted phenyl)amino-5-t-butylthiazoles (vi). ¹H-NMR (400 MHz, CDCl₃): δ 7.67–7.69 (d, 1H), 7.21–7.28 (d, 2H), 7.08–7.11 (m, 1H), 6.95–6.97 (m, 2H), 6.63–6.65 (m, 2H), 6.15 (s, 1H), 2.89–2.91 (m, 2H), 2.80–2.88 (m, 2H), 1.32 (s, 9H). MS (ESI⁺): 352.2 (M+H).

Example 51

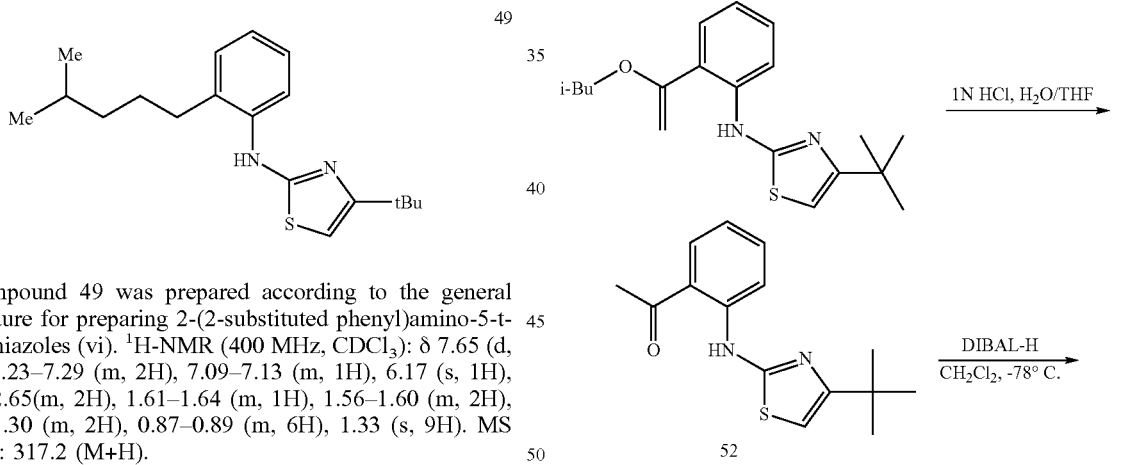

Compound 51 was prepared according to the general procedure for preparing 2-(2-substituted phenyl)amino-5-t-butylthiazoles (vi). ¹H-NMR (400 MHz, CDCl₃): δ 8.74–8.76 (m, 1H), 8.10 (d, 1H), 7.57–7.59 (m, 1H), 7.23–7.25 (m, 2H), 7.17 (m, 1H), 7.11–7.13 (m, 1H), 6.99–7.01 (m, 1H), 6.19 (s, 1H), 3.17–3.22 (m, 4H), 1.37 (S, 9H). MS (ESI⁺): 338.2 (M+H).

Example 53

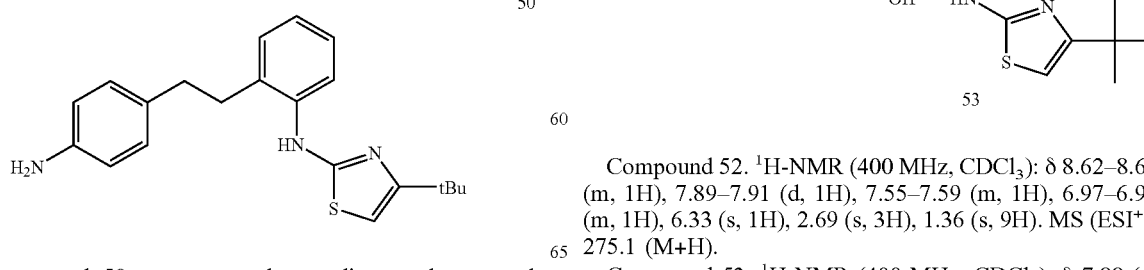

Compound 52. ¹H-NMR (400 MHz, CDCl₃): δ 8.62–8.64 (m, 1H), 7.89–7.91 (d, 1H), 7.55–7.59 (m, 1H), 6.97–6.98 (m, 1H), 6.33 (s, 1H), 2.69 (s, 3H), 1.36 (s, 9H). MS (ESI⁺): 275.1 (M+H).

Compound 53. ¹H-NMR (400 MHz, CDCl₃): δ 7.88 (d, 1H), 7.28–7.30 (m, 1H), 7.20–7.22 (m, 1H), 7.02–7.04 (m, 1H), 6.17 (s, 1H), 5.07–5.12 (m, 1H), 1.61–1.63 (d, 3H), 1.31 (s, 9H). MS (ESI+): 277.1 (M+H).

Example 54

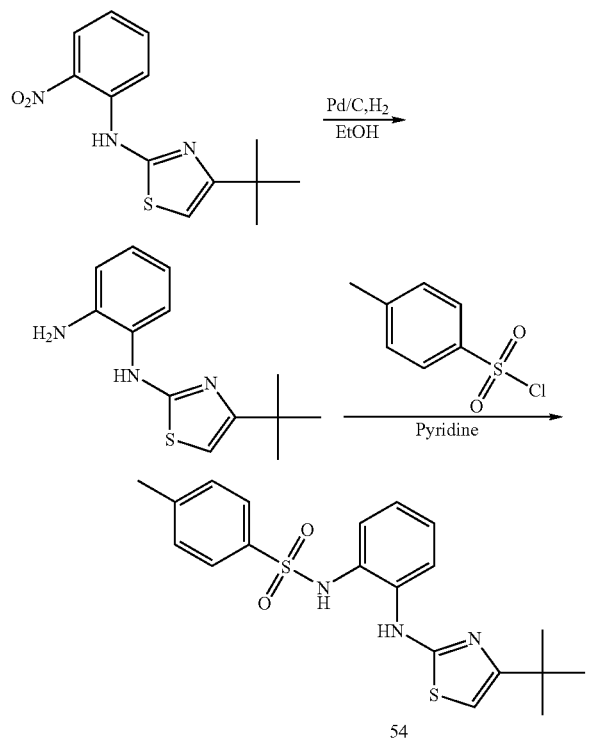

Compound 54 was prepared as outlined above. ¹H-NMR (400 MHz, CDCl₃): δ 7.73–7.75 (m, 2H), 7.28 (d, 1H), 7.22–7.24 (m, 2H), 7.13–7.16 (m, 2H), 6.69–6.71 (d, 1H), 6.24 (s, 1H), 2.38 (s, 3H), 1.32 (s, 9H) MS (ESI+): 402.1 (M+H).

Example 55

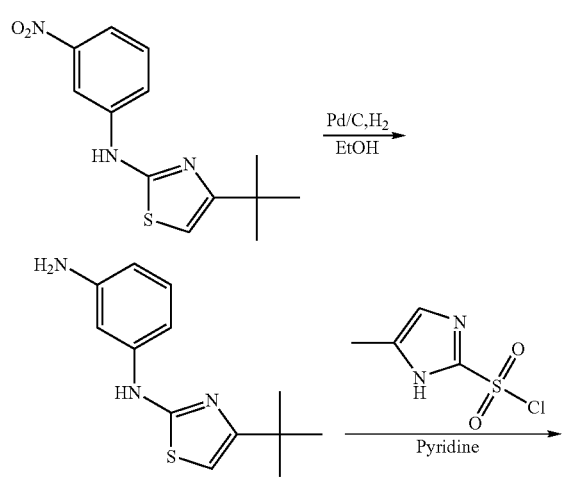

Compound 55 was prepared as outlined above. ¹H-NMR (400 MHz, CDCl₃): 7.76 (s, 1H), 7.77 (s, 1H), 7.32 (d, 1H), 7.09–7.13 (m, 1H), 6.71 (d, 1H), 6.41 (s, 1H), 3.66 (s, 3H), 1.34 (s, 9H). MS (ESI+): 392.1(M+H).

Example 56

Compound 56 was prepared as outlined above. ¹H-NMR (400 MHz, CDCl₃): δ 8.32 (d, 1H), 7.28–7.32 (m, 1H), 7.07 (d, 1H), 6.88–6.91 (m, 1H), 6.17 (s, 1H), 3.57 (s, 2H), 2.54 (m, 1H), 2.22 (s, 3H), 1.96 (m, 2H), 1.86 (m, 2H), 1.22–1.42 (m, 6H), 1.31 (s, 9H). MS (ESI+): 358.2 (M+H).

Example 57

This example illustrates a CCR4 binding assay that can be used for evaluating the compounds of the present invention.

Detection of Radiolabelled TARC and/or MDC Binding to CCR4

¹²⁵I-labelled TARC and MDC are available from commercial sources (e.g., Amersham-Pharmacia or Perkin Elmer Life Sciences). All buffers and materials are available from commercial sources (e.g., Gibco BRL, Sigma). To measure binding of ¹²⁵I-TARC or ¹²⁵I-MDC to cells expressing CCR4 (e.g., CEM cells, available from the ATCC), the ¹²⁵I-TARC or ¹²⁵I-MDC is diluted to a concentration of approximately 200 pM in a buffered saline solution (e.g., RPMI supplemented with 0.5% bovine serum albumin), and added to an equal volume of a suspension of cells (e.g., CEM cells at 5×10⁶ cells/mL). The resulting mixture is incubated for a period of time (e.g., 2 hours). The unbound $^{125}$I-TARC or $^{125}$I-MDC is separated from the cells by filtration, e.g., by passage through GF/B filter plate (Packard Biosciences) pre-treated with 0.3% polyethyleneimine (Sigma), using a Packard Filtermate 96 (Packard Biosciences). The amount of $^{125}$I-TARC or $^{125}$I-MDC retained with the cells on the filterplate is measured by adding a small amount of scintillation fluid (e.g., 50 μL of Microscint-20, obtained from Packard Biosciences), and reading scintillation on appropriate detection equipment, e.g., a Packard TopCount 383 (Packard Biosciences).

Non-specific binding of $^{125}$I-TARC or $^{125}$I-MDC can be estimated by measuring the amount of $^{125}$I-TARC or $^{125}$I-MDC retained with the cells on the filterplate when the assay is performed in the presence of a large excess of unlabelled TARC or MDC.

Inhibition of $^{125}$I-TARC or $^{125}$I-MDC binding to CCR4 is defined as a decrease in the retention of $^{125}$I-TARC or $^{125}$I-MDC to the cells on the filterplate.

The assay described above varies only moderately from standardly used procedures, e.g., Imai et al. (1997) *J. Biol. Chem.* 272:15036–15042, Imai et al. (1998) *J. Biol. Chem.* 273:1764–1768.

TABLE 1

CCR4 antagonist activity for compounds of the invention (inhibition of $^{125}$I-TARC binding).

| Compound | IC$_{50}$ (nM) |
|---|---|
| 12 | + |
| 2 | + |
| 11 | + |
| 4 | ++ |
| 9 | + |
| 10 | + |
| 1 | ++ |
| 3 | ++ |
| 13 | + |
| 5 | + |
| 19 | ++ |
| 8 | + |
| 15 | + |
| 6 | + |
| 18 | + |
| 7 | ++ |
| 20 | + |
| 21 | ++ |
| 24 | ++ |
| 35 | ++ |
| 45 | ++ |
| 49 | ++ |

+ denotes IC$_{50}$ > 1000 nM
++ denotes IC$_{50}$ < 1000 nM

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (I):

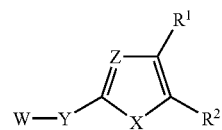

or a pharmaceutically acceptable salt or prodrug thereof, wherein
W is substituted indolyl;
X is S;
Y is N(R⁵);
Z is N;
R¹ is unsubstituted (C₁–C₈)alkyl or (C₁–C₈)alkyl substituted with NR'R" in which R' and R" are independently selected from the group consisting of aryl (C₁–C₄)alkyl and unsubstituted (C₁–C₈)alkyl, and wherein, optionally, R' and R" are combined with the nitrogen atom to which they are attached to form a 5-, 6- or 7-membered ring;
R² is H or (C₁–C₈)alkyl; and
optionally, R¹ and R² combine to form a 5- to 8-membered ring; and
R⁵ is selected from the group consisting of H, (C₁–C₈) alkyl, heteroatkyl, aryl and heteroaryl.

2. The compound of claim 1, wherein R¹ is unsubstituted (C₁–C₈)alkyl.

3. The compound of claim 1, wherein R¹ is (C₁–C₈)alkyl substituted with NR'R".

4. The compound of claim 1, having the formula:

5. A pharmaceutical composition comprising a pharmaceutically acceptable carrier or excipient and a compound of claim 1.

6. A method of treating an inflammatory condition or disease mediated by CCR4, comprising administering to a subject having the inflammatory condition or disease a therapeutically effective amount of a compound of claim 1, and wherein said inflammatory condition or disease is selected from the group consisting of allergic disease, psoriasis, atopic dermatitis, eczema, allergic rhinitis, asthma, inflammatory bowel disease, arthritis, multiple sclerosis and atherosclerosis.

7. The method of claim 6, wherein the inflammatory condition or disease is arthritis.

8. The method of claim 6, wherein the inflammatory condition or disease is an allergic disease.

9. The method of claim 6, wherein the inflammatory condition or disease is psoriasis, atopic dermatitis, or eczema.

10. The method of claim 6, wherein the inflammatory condition or disease is asthma.

11. The method of claim 6, wherein the inflammatory condition or disease is inflammatory bowel disease.

12. The method of claim 6, wherein the inflammatory condition or disease is multiple sclerosis.

13. The method of claim 6, wherein the inflammatory condition or disease is atherosclerosis.

14. The method of claim 6, wherein the subject is human.

15. A pharmaceutical composition comprising a pharmaceutically acceptable carrier or excipient and a compound of claim 2.

16. A pharmaceutical composition comprising a pharmaceutically acceptable carrier or excipient and a compound of claim 3.

17. A pharmaceutical composition comprising a pharmaceutically acceptable carrier or excipient and a compound of claim 4.

18. A method of treating an inflammatory condition or disease mediated by CCR4, comprising administering to a subject having said inflammatory condition or disease a therapeutically effective amount of a compound of claim 2 and wherein the inflammatory condition or disease is selected from the group consisting of allergic disease, psoriasis, atopic dermatitis, eczema, allergic rhinitis, asthma, inflammatory bowel disease, arthritis, multiple sclerosis and atherosclerosis.

19. The method of claim 18, wherein the inflammatory condition or disease is arthritis.

20. The method of claim 18, wherein the inflammatory condition or disease is an allergic disease.

21. The method of claim 18, wherein the inflammatory condition or disease is psoriasis, atopic dermatitis, or eczema.

22. The method of claim 18, wherein the inflammatory condition or disease is asthma.

23. The method of claim 18, wherein the inflammatory condition or disease is inflammatory bowel disease.

24. The method of claim 18, wherein the inflammatory condition or disease is multiple sclerosis.

25. The method of claim 18, wherein the inflammatory condition or disease is atherosclerosis.

26. The method of claim 18, wherein the subject is human.

27. A method of treating an inflammatory condition or disease mediated by CCR4, comprising administering to a subject having said inflammatory condition or disease a therapeutically effective amount of a compound of claim 3 and wherein the inflammatory condition or disease is selected from the group consisting of allergic disease, psoriasis, atopic dermatitis, eczema, allergic rhinitis, asthma, inflammatory bowel disease, arthritis, multiple sclerosis and atherosclerosis.

28. The method of claim 27, wherein the inflammatory condition or disease is arthritis.

29. The method of claim 27, wherein the inflammatory condition or disease is an allergic disease.

30. The method of claim 27, wherein the inflammatory condition or disease is psoriasis, atopic dermatitis, or eczema.

31. The method of claim 27, wherein the inflammatory condition or disease is asthma.

32. The method of claim 27, wherein the inflammatory condition or disease is inflammatory bowel disease.

33. The method of claim 27, wherein the inflammatory condition or disease is multiple sclerosis.

34. The method of claim 27, wherein the inflammatory condition or disease is atherosclerosis.

35. The method of claim 27, wherein the subject is human.

36. A method of treating an inflammatory condition or disease mediated by CCR4, comprising administering to a subject having said inflammatory condition or disease a therapeutically effective amount of a compound of claim 4 and wherein the inflammatory condition or disease is selected from the group consisting of allergic disease, psoriasis, atopic dermatitis, eczema, allergic rhinitis, asthma, inflammatory bowel disease, arthritis, multiple sclerosis and atherosclerosis.

37. The method of claim 36, wherein the inflammatory condition or disease is arthritis.

38. The method of claim 36, wherein the inflammatory condition or disease is an allergic disease.

39. The method of claim 36, wherein the inflammatory condition or disease is psoriasis, atopic dermatitis, or eczema.

40. The method of claim 36, wherein the inflammatory condition or disease is asthma.

41. The method of claim 36, wherein the inflammatory condition or disease is inflammatory bowel disease.

42. The method of claim 36, wherein the inflammatory condition or disease is multiple sclerosis.

43. The method of claim 36, wherein the inflammatory condition or disease is atherosclerosis.

44. The method of claim 36, wherein the subject is human.

* * * * *